US006692767B2

(12) United States Patent
Burnside et al.

(10) Patent No.: US 6,692,767 B2
(45) Date of Patent: *Feb. 17, 2004

(54) SOLID SOLUTION BEADLET

(75) Inventors: Beth A. Burnside, Silver Spring, MD (US); Charlotte M. McGuinness, Bethesda, MD (US); Edward M. Rudnic, North Potomac, MD (US); Richard A. Couch, Bethesda, MD (US); Xiaodi Guo, Derwood, MD (US); Alexander K. Tustian, Bothell, WA (US)

(73) Assignee: Shire Laboratories Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 115 days.

(21) Appl. No.: 09/156,464

(22) Filed: Sep. 18, 1998

(65) Prior Publication Data

US 2001/0006650 A1 Jul. 5, 2001

Related U.S. Application Data

(60) Provisional application No. 60/059,408, filed on Sep. 19, 1997.

(51) Int. Cl.[7] .............................. A61K 9/16; A61K 9/20; A61K 9/48
(52) U.S. Cl. ....................... 424/489; 424/464; 424/465; 424/451; 424/435; 424/490; 514/772.3; 514/784; 514/785; 514/786; 514/951; 514/770
(58) Field of Search ................. 424/464, 468, 424/469, 474, 480, 482, 489, 490, 502, 501, 499, 435, 451

(56) References Cited

U.S. PATENT DOCUMENTS

| 3,857,933 | A | * | 12/1974 | Ross et al. | |
|---|---|---|---|---|---|
| 4,880,634 | A | * | 11/1989 | Speiser | |
| 5,213,810 | A | | 5/1993 | Steber | ......................... 424/490 |
| 5,340,588 | A | | 8/1994 | Domb | ......................... 424/450 |
| 5,430,021 | A | | 7/1995 | Rudnic et al. | ................. 514/14 |
| 5,807,583 | A | * | 9/1998 | Kristensen et al. | |

FOREIGN PATENT DOCUMENTS

| EP | 448930 A1 | | 10/1991 |
|---|---|---|---|
| JP | 11-502201 | * | 2/1999 |
| WO | 91/07171 | | 5/1991 |
| WO | 94/12180 | | 6/1994 |
| WO | 94/27557 | | 12/1994 |

OTHER PUBLICATIONS

Deasy, Patrick B., "Spray Drying, Spray Congealing, Spray Embedding, and Spray Polycondensation," *Microencapsulation and Related Drug Processes*, Marcel Dekker, Inc. NY:181–193 (1984).

(List continued on next page.)

*Primary Examiner*—James M. Spear
(74) *Attorney, Agent, or Firm*—Mary Elisa Lane

(57) ABSTRACT

Disclosed is a beadlet comprising (i) a hydrophobic long chain fatty acid or ester material; (ii) a surfactant; and (iii) a therapeutic agent which in admixture form a solid solution at room temperature. The hydrophobic material preferably has a melting point of about 40 to about 100° C., and is most preferably glyceryl behenate. The surfactant is preferably a polyglycolyzed glyceride, polyoxyethylene sorbate, ethylene or propylene block copolymer or combinations thereof, and is most preferably polyoxyethylene 20 sorbitan monolaurate.

23 Claims, 19 Drawing Sheets

Labrasol 20%

OTHER PUBLICATIONS

Eldem, et al., "Optimization of Spray–Dried and –Congealed Lipid Micropellets and Characterization of Their Surface Morphology by Scanning Electron Microscopy," *Pharmaceutical Research*, 8(1):47–54 (1991).

Eldem, et al., "Polymorphic Behavior of Sprayed Lipid Micropellets and Its Evaluation by Differential Scanning Calorimetry and Scanning Electron Microscopy," *Pharmaceutical Research*, 8(2):178–184 (1991).

Hincal, A.A. and Kas, H. S., "Preparation of Micropellets by Spray Congealing," *Multiparticulate Oral Drug Delivery Ghebre–Sellassie (Ed.), Marcel Dekker, Inc. NY*:17–34 (1994).

Kennedy, J.P. and Niebergall, P.J., "Development and Optimization of a Solid Dispersion Hot–Melt Fluid Bed Coating Method," *Pharmaceutical Development and Technology*, 1(1):51–62 (1996).

* cited by examiner

SOLID SOLUTION BEADLET

This application is based on U.S. application Ser. No. 60/059,408 filed Sep. 19, 1997, the priority of which is claimed.

The present invention relates to the field of pharmaceutical delivery formulations and, more particularly, to those providing rapid release of the therapeutic agent upon oral delivery.

BACKGROUND OF THE INVENTION

A variety of methods for forming micropellets are known in the art. See Kennedy and Niebergall, Development and Optimization of a Solid Dispersion Hot-Melt Fluid Bed Coating Method, Pharmaceutical Development and Technology, 1(1):51–62(1996); Hincal and Kas, Preparation of Micropellets by Spray Congealing, in Multiparticulate Oral Drug Delivery, Ghebre-Sellassie (Ed.), Marcel Dekker, Inc. NY, pgs. 17–34 (1994); Eldem et al., Polymorphic of Sprayed Lipid Micropellets and its Evaluation by Differential Scanning Calorimetry and Scanning Electron Microscopy, Pharmaceutical Research, 8(2):178–184 (1991); Eldem et al., Optimization of Spray Dried and -Congealed Lipid Micropellets and Characterization of Their Surface Morphology by Scanning Electron Microscopy, Pharmaceutical Research, 8(1):47–54 (1991); and Deasy, Spray Drying, Spray Congealing, Spray Embedding and Spray Condensation, in Microencapsulation and Related Drug Processes, Marcel Dekker, Inc., NY, pgs. 181–193 (1984).

SUMMARY OF THE INVENTION

In accordance with an aspect of the present invention, there is provided a composition including at least one therapeutic agent and a pharmaceutically acceptable carrier in the form of a solid beadlet wherein the beadlet includes a acceptable carrier in the form of a solid beadlet wherein the beadlet includes a combination of at least one hydrophobic long chain fatty acid or fatty acid ester and at least one surfactant. The hydrophobic long chain fatty acid or ester thereof and surfactant are present in the beadlet as a solid solution. The therapeutic agent is dispersed in the solid beadlet and is present in the composition in a therapeutically effective amount, with such amount generally being at least 0.001%, by weight, of the composition.

The hydrophobic long chain fatty acid or ester thereof is generally present in an amount of at least 20% with such material in most cases being present in an amount no greater than 97%, by weight.

The beadlet(s) generally has a particle size that does not exceed 1000 microns. In most cases, the particle size is at least 50 microns. In one embodiment, the particle size does not exceed 500 microns. In another embodiment, the particle size is from 100 to 350 microns.

In a preferred embodiment, the surfactant is one that is liquid at room temperature in that a liquid surfactant in the composition of the invention provides for improved drug delivery.

The surfactant may comprise at least 3% of the core beadlet formulation and in many cases exceeds 10% of the core beadlet formulation all by weight.

The beadlet is preferably in the form of a solid solution wherein the therapeutic agent is dissolved in the hydrophobic material.

In one aspect, the invention provides a solid solution beadlet (used synonymously with granule or particle) comprising (i) at least about 20% by weight of a hydrophobic long chain fatty acid or ester material; (ii) from about 3% to about 40% by weight of a surfactant; and (iii) from about 1% to about 70% by weight of a therapeutic agent, which in admixture form a solid solution at room temperature.

The long chain acids used as an acid or ester generally include at least 12 carbon atoms and generally do not include more than 22 carbon atoms. The acids may be saturated or unsaturated and generally are aliphatic long chain acids. When used as an ester, the ester is preferably a glycerol ester. The ester may be a mono-, di or tri-ester of glycerol.

The hydrophobic material is preferably oleic acid, gadoleic acid, eurcic acid, linoleic acid, linolenic acid, ricinoleic acid, riachidonic acid, glycerol esters of the foregoing acids, or glycerol behenate.

The hydrophobic material preferably has a melting point of from about 40 to about 150° C., and is most preferably glyceryl behenate (e.g. Compritol™ from Gattefosse Inc., France). The surfactant is preferably selected from the group consisting of polyglycolyzed glycerides, polyoxyethylene sorbates, ethylene or propylene block copolymers or combinations thereof, and is most preferably polyoxyethylene 20 sorbitan monolaurate or Labrasol®, a polyglycolized glyceride (Gattefosse, France). The beadlet can further include sodium $C_9$–$C_{30}$ alkyl sulfate or citric acid. The beadlet can also contain a glidant (such as fumed silicon dioxide) to improve tabletting properties. Typically preferred therapeutic agents include acyclovir, acyclovir and at least one additional antiviral agent, dihydroergotamine or methylphenidate.

In another preferred embodiment the beadlets are coated with an immediate release coating, such as Opadry®I (hydropropylmethylcellulose, i.e., HPMC) and Opadry®-II (HPMC, maltodextrin and propyleneglycol) from Colorcon, Inc. (West Point, Pa.) or Aquateric® (cellulose acetate phthalate enteric polymer) from FMC, Inc. (Philadelphia, Pa.).

Another embodiment provides pharmaceutical compositions of a plurality of coated or uncoated single phase solid solution beadlets in a pharmaceutically acceptable carrier. The composition can be, for example, in the form of a tablet (optionally coated, such as with an enteric coating), buccal tablet, sublingual tablet, capsule or other oral dose delivery forms.

The oral delivery form can also be coated, if desired, with various protective coating materials or with materials that control the rate or location of release in the patient. This can be done by known methods using such known materials.

DETAILED DESCRIPTION OF THE PREFERRED EMBODIMENTS

Figure 1:
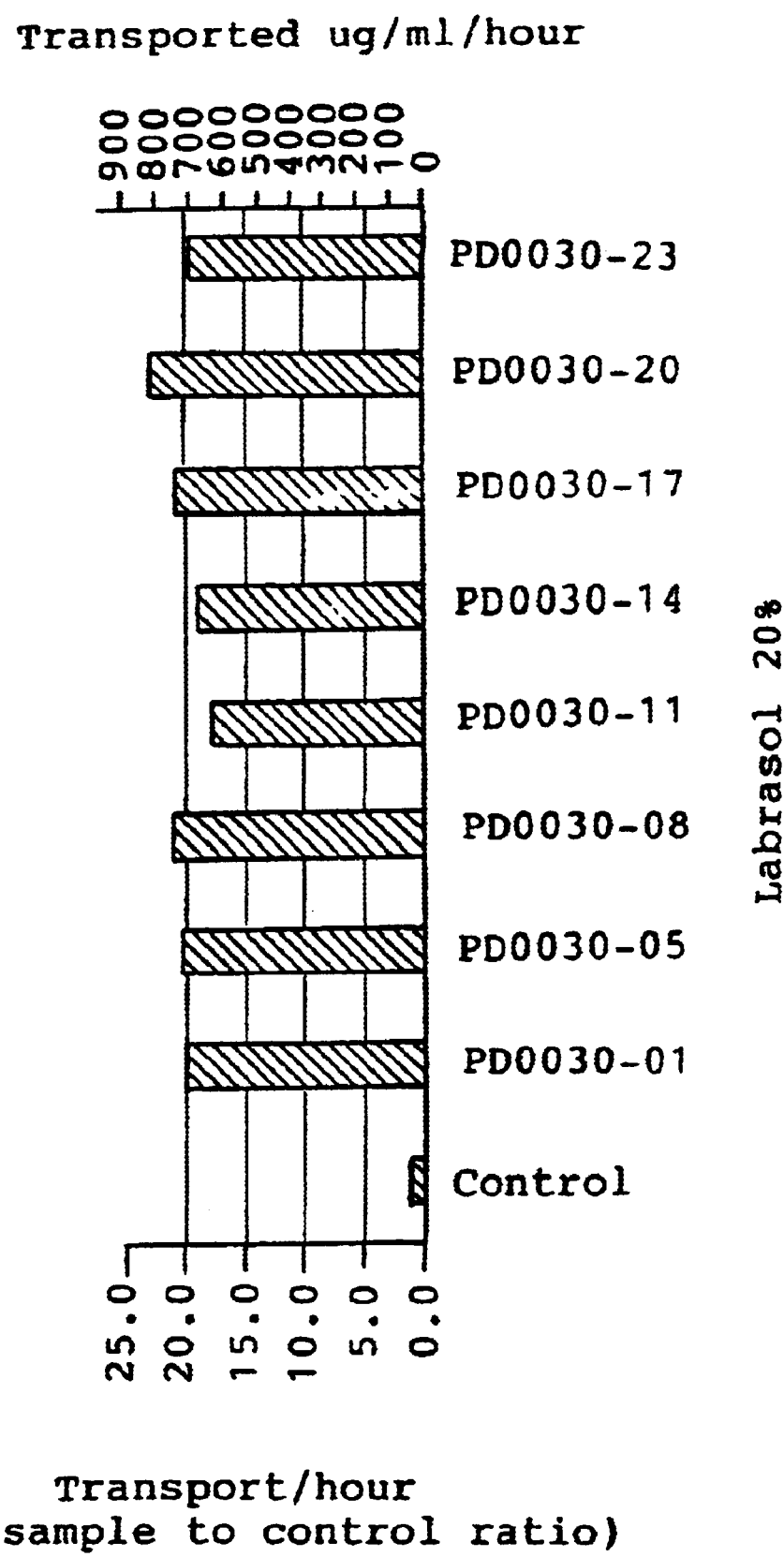
FIG. 1 is a plot of acyclovir transport through a Caco-2 cell monolayer using several of the Formulations described in Example 1.

The delivery system of the invention can be used to provide rapid controlled release of any of a broad variety of therapeutically active agents. Examples include the following: cough suppressants, such as dextromethorphan hydrobromide and codeine; antibiotics such as cephalosporin; antihistamines such as chlorpheniramine maleate, brompheniramine maleate, loratidine, astemizole, diclofenac sodium and terfenadine; decongestants such as pseudoephedrine and phenylephrine; antihypertensives such as ACE-inhibitors, verapamil, nifedipine, propanolol, metoprolol, metoprolol succinate, metoprolol fumarate, metoprolol, methylphenadate, tartarate; agents to treat attention deficit disorder/hyperactivity such as methylphenadate, d and/or l isomers of methylphenadate, amphetamines, d and/or l isomers of amphetamines, and combinations of amphetamines; calcium channel blockers such as verapamil, diltiazam, nifedipine, nimodipine, felodipine, nicardipine, isradipine and amlodipine; antidiabetic agents such as glipizide and ibromectin; proton pump inhibitors such as omeprazole; anti-convulsants and anti-epileptics such as valproate sodium, clonazepam, gabapetin, and topiramate; antidepressives such as buspirone, fluoxeline, 5-hydroxytryptamine receptor agonist and antagonist; anti-migraines such as sumatreptan and dihydroergotamine; antipsychotics such as resperidone; antiemetics such as ondansetron; anti-heartburns such as cisapride; H2 receptor antagonists such as cimetidine, ranitidine, famotidine, nizatidine; carbamazepine; beta adrenergic receptor blockers; anti-Parkinson agents such as selegiline, carbidopa/levodopa, pergolide, bromocriptine, amantadine, trihexyphenidyl HCl; antiviral agents including antiherpesvirus agents such as acyclovir, famciclovir, valcyclovir, foscamet, ganciclovir; antiretroviral agents such as didanosine, stavudine, zalcitabine, zidovudine; and others such as amantadine, interferon alpha, ribavirin, rimantadine; anti Alzheimer's agents such as galantamine; and other therapeutic agents such as cimetidine, propiomazine, phenytoin, tacrine, propiazam, proplazam; vinca alkaloid.

Also contemplated are other therapeutic polypeptides and proteins, including fragments, analogs and mimetics thereof, and prodrugs which possess the same therapeutic activity, to at least a therapeutically useful extent, such as vasopressin, desmopressin, LHRH, luprolide, buserelin, calcitonin, insulin, parathyroid hormone, growth hormone(s) and erythropoietin. Further, examples include cyclosporin, angiotensin I, II and III, encephalins, enkephalins and their analogs, ACTH, antiinflammatory peptides I, II, III, bradykinin, cholecystikinin (CCK) fragments 26–33 and 30–33, pre/pro CCK (V-9-M), β-endorphin, dinorphin, leucokinin, leutinizing hormone releasing hormone (LHRH), neurokinins (e.g. neurokinin A), somatostatin, substance P, thyroid releasing hormone (TRH), vasopressin, fibrinogen receptor antagonists (arginine-glycine-aspartic acid containing peptides) which are platelet aggregation antagonists or inhibitors, growth hormone releasing peptides (GHRP), insulin, LH-RH releasers and inhibitors, endothelins, glutamate or kainic acid neuro-excitation or neuro-toxicity inhibitors, GPIIb/IIIa receptor blockers such as the prodrug orbofiban, atrial natreutetic factor, gastrin, cytoprotectives, MSH modulators, or elastase or growth factors and cytokines, renin inhibitors, and HIV protease inhibitors.

Therapeutic agents can also include immunoactive agents selected from peptides, proteins, glycopolysaccharides and glycoproteins and fragments and analogs thereof, which possess the ability to suppress or eliminate immune responses thereto. Active analogs include compounds which have at least 90% structural homology to the proteins or to the active fragments. As such, the term includes, without limitations, any combination of their polypeptide domains or fragments possessing the ability to eliminate or suppress immune responses to the protein upon oral administration such as is used for replacement therapy. Examples of polypeptides include hormones, such as insulin; polypeptides to supplement a deficiency in production of a physiologically important polypeptide, such as hematologic regulatory factor; or cell or tissue preparations such as allogeneic or xenogeneic tissue or cells.

Therapeutic agents can also include immunoactive agents that can suppress or eliminate an immune response against allergens, particularly in cases of hypersensitivity caused by allergens, e.g. Type IV cell-mediated (delayed type) hypersensitivity. Also included are vaccines, especially those yielding mucosal immunity.

Therapeutic agents can also include those intended to be locally active in the gastrointestinal tract, such as therapeutics intended to treat Inflammatory Bowel Disease or Krohn's Disease, including corticosteroids such as beclomethasome dipropionate, budesonide, flunisolide, cromolyn, and nedocromil sodium.

Several methods are known in the art for the formation of beadlet/granule particles, both in uncoated and coated forms. The experiments reported in the Examples set forth below were performed using three of these methods: (i) a spray congealing method; (ii) a hot-melt method; and (iii) a spray-melt method. Each can be scaled in accordance with the stage of development.

The spray-congealing method begins with melting a typical pharmaceutically acceptable long chain alkyl-based wax that has a melting point of greater than or equal to about 55° C. Examples include stearic acid wax, glyceryl fatty acid esters (e.g. Compritol® brand), glyceryl monostearate or lauric acid wax. The melted wax is then mixed in a suitable mixing vessel, with the active pharmaceutical agent (usually 50–100 microns) and all other components of the beadlet composition, except for flow aids as described below. The mixture is sprayed into a spray-congeal tower or fluid bed processor. A flow of cool air is passed through the tower to solidify the beadlets. After the solidified beadlet has been formed, flow aids are added to prevent beadlet sticking, i.e. to make the beadlet surfaces more slippery, resulting in finished uncoated beadlets prepared by this method.

The hot-melt method is performed in a fluid bed, which takes the form of a vertical cylinder resting in a bowl-shaped base (one such device used in the Examples is the Wurster inserted in a Glatt GPCG5 fluid bed). The side walls of the cylinders have a number of spray nozzle entry ports along their length. A dry powder particulate mixture of the beadlet components, except for the wax and lubricant(s), is placed in the bowl and a metered flow of air is introduced into the cylinder. This raises the powder particles into the cylinder forcing a controlled flow pattern of the powder particles within at least one portion of the height of the cylinder. Then, melted wax and lubricant are introduced through some of these same nozzles, particularly the upper nozzles in an embodiment called the "top spray" method. The lower nozzles continue to introduce cool air from below to effect solidification of beadlets containing the powder, wax and lubricant components. The "top spray" method is used in several of the Examples presented herein.

The spray-melt method is also performed in a fluid bed. Solid ingredients (including wax that is solid at room temperature) i.e. not including liquid surfactants or solubilizing agents, are placed in a suitably configured fluid bed. Liquid surfactants, mixtures thereof and/or solubilizing agents are then sprayed onto the solid ingredients already in the fluid bed. This results in particles which are actually separate but attached drug, wax and surfactant components. These separate-component particles are heated sufficiently to soften the wax, resulting in homogeneous particles which are then cooled to result in solidified beadlets. Several formulations in the Examples were prepared this way.

The composition or preparation of the invention can further include a surfactant, or a mixture of two or more surfactants. A surfactant is an amphiphilic molecule consisting of a hydrophobic tail and a hydrophilic head. These molecules possess distinct regions of both hydrophilic and hydrophobic character. The hydrophobic tail can be a hydrocarbon or fluorocarbon chain of 8 to 18 carbon atoms. They are long chain molecules such as, for example, soaps or detergents. Surfactants accumulate at the hydrophilic/hydrophobic (water/oil) interface and lower the surface tension at the interface. One effect of a reduced surface tension is the stabilization of the emulsions. This is because molecules with both polar and non-polar groups become oriented such that the hydrocarbon tail embeds itself into the hydrophobic phase and the hydrophilic head protrudes into the hydrophilic phase. Where the hydrophobic composition or other component of the preparation includes a surface-active agent, such as a surfactant, it is usually present in amounts of about 3% to 50.0% weight/weight of the beadlet or granule composition with a preferred range of 3% to 10% (w/w). Preferred surfactants include, for example, the Tween (polyoxyethylene sorbate) family of surfactants (ICI, Wilmington, Del.), the Span (sorbitan long chain carboxylic acid esters) family of surfactants (ICI), the Pluronic (ethylene or propylene oxide block copolymers) family of surfactants (BASF, Parsippany, N.J.), the Labrasol, Labrafil and Labrafac (each polyglycolyzed glycerides) families of surfactants (GatteFossé, St. Priest, France), sorbitan esters of oleate, stearate, laurate or other long chain carboxylic acids, poloxamers (polyethylene-polypropylene glycol block copolymers), other sorbitan or sucrose long chain carboxylic acid esters, mono and diglycerides, PEG derivatives of caprylic/capric acid triglycerides and mixtures thereof. Representative preferred surfactants are polymer 124, a polyglycolized glyceride, sorbitan laurate, polyoxyethlyene (20) sorbitan monooleate.

Coating of the beadlets formed by any of the above methods is achieved as follows. An aqueous solution of an "immediate release" coating is formed and sprayed onto the beadlets substantially immediately after they have been formed, using the same apparatus and same nozzles by which the beadlets were formed. A list (non-limiting) of release coating materials and suppliers is provided in Table 1 below. At this point, more flow aid may be introduced briefly. The beadlets are then discharged to a blender (such as a Patterson-Kelly V-blender).

Major fluid bed processors and suppliers include Aeromatic and Multiprocessor series (Niro Inc., Columbia, Md. 21045); GPCG series (Glatt Air Techniques, Inc., Ramsey, N.J. 07446); Vector fluid bed series (Vector Corporation, Marion, Iowa 52302); and Kugel Coater series (Huttlin, Coating-Technik GmbH, Steinen, Germany).

TABLE 1

Major Immediate Release Coating Material and Suppliers

| Brand name | Ingredients | Manufacturer |
| --- | --- | --- |
| Opadry ®I | HPMC, PEG & pigment | Colorcon, West Point, PA |
| Opadry II ® | HPMC, PEG, maltodextrin & pigment | Colorcon, West Point, PA |
| Klucel | Hydroxypropyl cellulose | Hercules/Aqualon, Wilmington, DE |
| Natrosol | Hydroxyethyl cellulose | Hercules/Aqualon, Wilmington, DE |
| Kollidon | Polyvinyl pyrrolidone | BASF, Parsippany, NJ |
| Kelton | Sodium alginate | Kelco, San Diego, CA 92123 |
| Pharmaceutical gelatin | Gelatin | Hormel Foods Corp., Austin, MN |

The beadlets can be incorporated into hard gelatin capsules, either with additional excipients, or alone. Typical excipients to be added to a capsule formulation include, but are not limited to: fillers such as microcrystalline cellulose, soy polysaccharides, calcium phosphate dihydrate, calcium sulfate, lactose, sucrose, sorbitol, or any other inert filler. In addition, there can be flow aids such as fumed silicon dioxide, silica gel, magnesium stearate, calcium stearate or any other material imparting flow to powders. Because of their hydrophobic nature, the particles should not need a lubricant, but one can be added if necessary by using polyethylene glycol, leucine, glyceryl behenate, magnesium stearate or calcium stearate.

The beadlets can also be incorporated into a tablet, in particular by incorporation into a tablet matrix, which rapidly disperses the particles after ingestion. In order to incorporate these particles into such a tablet, a filler/binder must be added to a tablet that can accept the particles, but will not allow their destruction during the tableting process. Materials that are suitable for this purpose include, but are not limited to, microcrystalline cellulose (Avicel), soy polysaccharide (Emcosoy), pregelatinized starches (STARCH 1500, National 1551), and polyethylene glycols (Carbowax). The materials should be present in the range of 5–75% (w/w), with a preferred range of 25–50% (w/w).

In addition, disintegrants are added in order to disperse the particles once the tablet is ingested. Suitable disintegrants include, but are not limited to: cross-linked sodium carboxymethyl cellulose (Ac-Di-Sol), sodium starch glycolate (Explotab, Primojel), and cross-linked polyvinylpolypyrrolidone (Plasdone-XL) These materials should be present in the range of 3–15% (w/W), with a preferred range of 5–10% (w/w).

Lubricants are also added to assure proper tableting, and these can include, but are not limited to: magnesium stearate, calcium stearate, stearic acid, polyethylene glycol, leucine, glyceryl behenate, and hydrogenated vegetable oil. These lubricants should be present in amounts from 0.1–10% (w/w), with a preferred range of 0.3–3.0% (w/w).

Tablets are formed, for example, as follows. The particles are introduced into a blender along with Avicel, disintegrants and lubricant, mixed for a set number of minutes to provide a homogeneous blend which is then put in the hopper of a tablet press with which tablets are compressed. The compression force used is adequate to form a tablet; however, not sufficient to fracture the beads or coatings.

The tablets can also be coated with conventional coatings known for a variety of effects, e.g. enteric, immediate or sustained release.

Caco-2 Cell Monolayer Testing of Drug Transport

We have used a cell culture based model to test formulations to improve intestinal adsorption of poorly adsorbed drugs. This allows testing of transport through intestinal epithelium without the influence of gastric hydrolysis or enzyme degradation in the GI tract, blood, or liver. It further allows simultaneous testing of multiple different formulations.

The Caco-2 cell line is derived from human colon cancer cells. They are epithelial-type cells that differentiate, in culture, into cell monolayers that are extremely similar to normal fetal intestinal epithelium. Intestinal epithelium is the cell type that lines the intestine. It has very specific adsorptive and barrier properties to allow absorption of nutrients but prevent passage of most of the intestinal contents. Two important characteristics of intestinal epithelium are the brush border, which forms the luminal surface of the epithelium, and the tight junctions, which are impenetrable fusions between cells. The brush border is important because it produces the enzymes and specialized membrane structures that allow cells to selectively absorb important nutrients such as glucose; tight junctions are important because they form continuous connection between cells and allow the epithelium to exclude unwanted molecules. Caco-2 cells, as used in our assays, display both of these characteristics.

Caco-2 colon carcinoma cells were obtained from the American Tissue Culture Collection (Rockville, Md.) and maintained in culture in high glucose DMEM with 10% fetal calf serum, plus pen/strep, at 37° C., in 5% $CO_2$. Cells are subcultured roughly every 5–7 days, 1:3 in T75 flasks, or when cells are 80–90% confluent, as determined by visual inspection. Caco-2 cells are adherent and are disassociated from the surface of the flask by incubation at room temperature with 0.25% trypsin in Hank's balanced salt solution (HBSS) without calcium or magnesium. Caco-2 cells are contact inhibited and when they become confluent, begin to differentiate and lose the capacity to undergo mitosis. To maintain a consistent genotype, it is important to avoid selecting for a subset of cells that is not differentiated. This is done by subculturing working stocks of cells before they differentiate. Initial experiments establish the time course of differentiation.

Transport studies use differentiated cells, which are cells that have acquired many of the characteristics of normal intestinal epithelium including a brush border and barrier properties. Transport experiments use 2.45 cm Transwell cell culture inserts with 3.0 $\mu$m pores (Costar, Boston, Mass.). These are plastic inserts for tissue culture wells, which allow a distinct apical and basal compartment only connected by small pores on the growing surface. Cells are seeded on the upper surface of the insert at $3\times10^5$ cells per well and media changed every day. Media was changed in the lower compartments by lifting insert with a sterile forceps. The upper compartment holds 1.5 ml, and the lower 2.6 ml. Tissue culture reagents can be purchased from GIBCO-Life Technologies (Gaithersburg, Md.) or Biofluids (Rockville, Md.).

Transport studies usually include polyethylene glycol (PEG) 4000 as a large, nonreactive, reference molecule, which would not permeate normal epithelium, and the following test peptides, which have a range of molecular weights and hydrophilicitys: thyrotrophin releasing hormone (TRH) (MW=362.15), DAGO-enkephalin (MW= 513.26) and [ARG8-] vasopressin (MW=1083.41). Glucose transport is also measured using $^3$H and $^{14}$C labeled D- and L- glucose. Unlabeled peptides can be purchased from Peninsula Laboratories, Belmont, Calif. Tritium-labeled peptides and glucose and $^{14}$C-PEG can be purchased from NEN-DuPont, Boston, Mass., or Amersham Corp., Arlington Heights, Ill.

For transport determinations unlabeled peptides, concentration 10 mM, and labeled, concentration of 1 μCi per ml and transport enhancers, are added to HBSS plus calcium and magnesium. Transport media, containing peptide or glucose plus labeled and unlabeled PEG, is added to the upper compartment of the Transwell, where the test solution is in contact with the apical surface of the cells. Transport is measured by taking aliquots from the lower compartment, which is in contact with the basal surface of the cells. Studies are performed in a six-well tissue culture plate and Transwells are moved to a new well every twenty minutes, giving determinations for two hours. An aliquot of media is removed from the upper and lower compartments, scintillation cocktail is added (NEN DuPont) and the total radioactivity from the upper and lower compartments is calculated. Transport is calculated as percent transport per hour from top to bottom. Because in all experiments the amount of peptide in the upper compartment is large compared to the amount transported, no correction is made for loss of peptide in the upper compartment with time. Radioactivity is measured in a Wallac or Beckman scintillation counter.

The following examples further illustrate the invention but are not limitations of its scope.

EXAMPLE 1

Uncoated Single Phase Solid Solution Beadlets p
Uncoated beadlets were prepared, as described above and in Table 2, to have the formulations set forth in Table 2.

TABLE 2

Uncoated Beadlet Formulations

| Formulation | PD0030-01 | PD0030-05 | PD0030-08 | PD0030-11 |
|---|---|---|---|---|
| Core Formulation | | | | |
| Acyclovir USP 30 μm | 35 | 25 | 35 | — |
| Acyclovir-micronized | — | — | — | 35 |
| Labrasol | 20 | 20 | 20 | 20 |
| Compritol 888 ATO | 40 | 55 | 40 | 40 |
| Talc | 5 | 0 | 5 | 5 |
| Total | 100 | 100 | 100 | 100 |
| Core Preparation | Spray-melt | Spray-cong | Hot-melt | Spray-melt |
| Form | Granules | Beadlets | Granules | Granules |
| Size | ~300 μm | <100 μm | ~250 μm | ~200 μm |

Table 2 demonstrates that acyclovir beadlets can be prepared by a variety of methods. Acyclovir, USP or micronized acyclovir can be used. The particle size of original drug does not affect the beadlet formation.

TABLE 3

Additional Uncoated Beadlet Formulations

| Formulation | PD0030-14 | PD0030-17 | PD0030-20 | PD0030-23 |
|---|---|---|---|---|
| Core Formulation | | | | |
| Acyclovir USP | — | 35 | — | — |
| Acyclovir-micronized | 35 | — | 35 | 35 |
| Labrasol | 20 | 20 | 25 | 25 |
| Compritol 888 ATO | 40 | 42 | 37 | 33 |
| SLS | — | 1 | 1 | 1 |
| Citric Acid | — | 1 | 1 | 1 |
| Talc | 5 | 1 | — | 5 |
| Cab-O-Sil | — | — | 1 | — |
| Total | 100 | 100 | 100 | 100 |
| Core Preparation | Hot-melt | Spray-cong | Spray-melt | Spray-melt |
| Form | Granules | Beadlets | Granules | Granules |
| Size (estimated) | ~200 μm | <100 μm | large | large |

When increasing amounts of Labrasol go to 25%, the beadlet size is increased and the process has to be optimized to obtain desired beadlet size. The addition of 5% talc does not change the particle size of beadlets significantly.

TABLE 4

Acyclovir Transport Through Caco-2 Cell Monolayers

| Formulation | Initial Conc.(mg/ml) | Transport μg/ml/hr | Transport sample/control ratio |
|---|---|---|---|
| CONTROL | 46.6 | 40 | 1.0 |
| PD0030-01 | 46.6 | 718 | 18.0 |
| PD0030-05 | 33.3 | 731 | 18.3 |
| PD0030-08 | 46.6 | 751 | 18.8 |
| PD0030-11 | 46.6 | 648 | 16.3 |
| PD0030-14 | 33.3 | 686 | 17.2 |
| PD0030-17 | 46.6 | 746 | 18.7 |
| PD0030-20 | 46.6 | 827 | 20.7 |
| PD0030-23 | 33.3 | 701 | 17.6 |

Beadlets having these Formulations were tested for drug transport in the Caco-2 cell monolayer model described above. The results are reported in Table 4 and also in FIG. 1.

Figure 2:
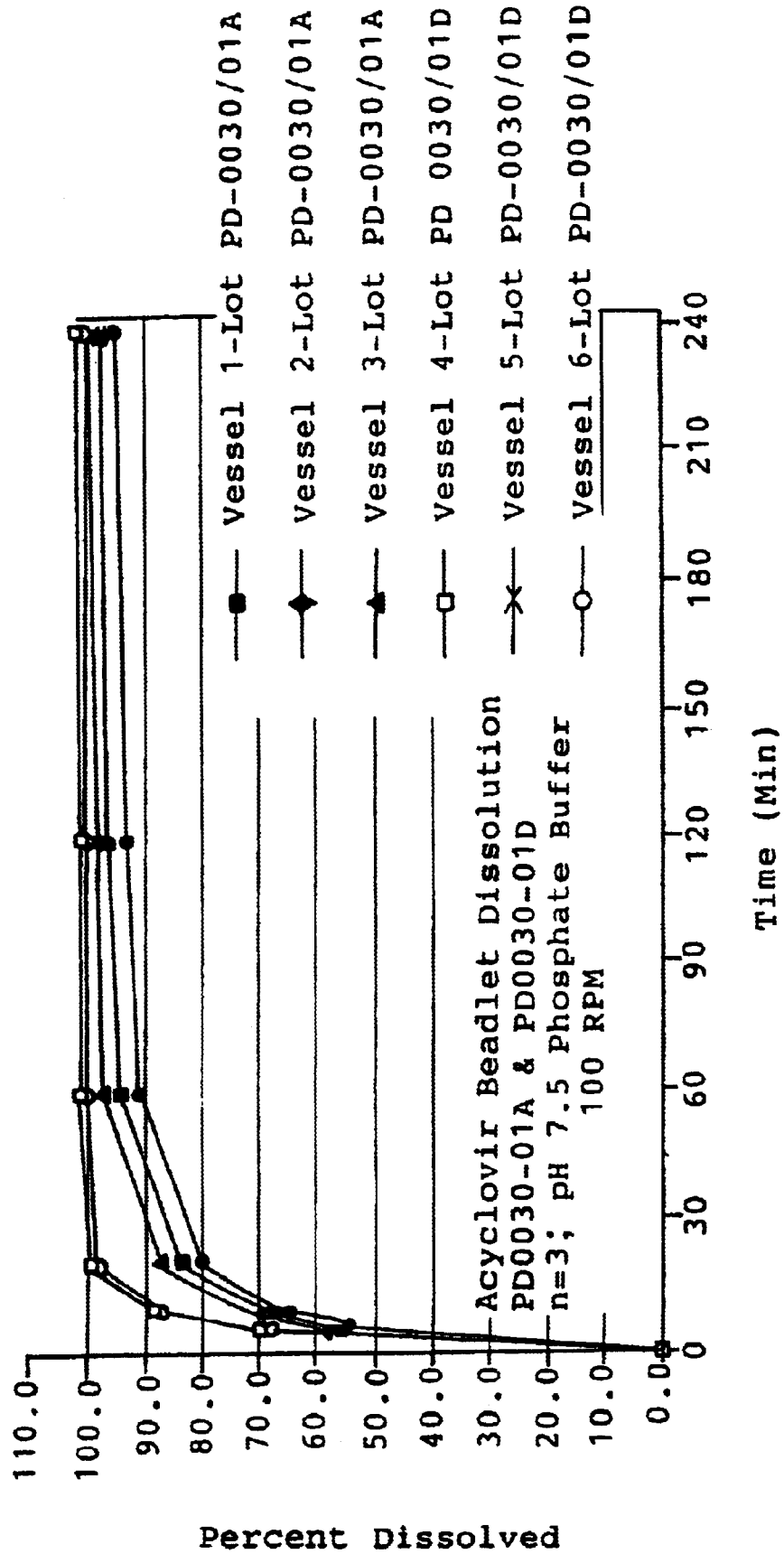
FIG. 2 is a plot of acyclovir-containing beadlet percent dissolution over time for two of the Formulations from Example 1. It illustrates the immediate release acyclovir dissolved (%) over time from beadlets containing high percentages of glyceryl behenate and Labrasol®.

FIG. 2 is a plot of acyclovir-containing beadlet percent dissolution over time for two of the Formulations from this Example (PD0030-01A and PD0030-01D). It illustrates the immediate release acyclovir dissolved (%) over time from beadlets containing high percentages of glyceryl behenate and Labrasol®.

Figure 3:
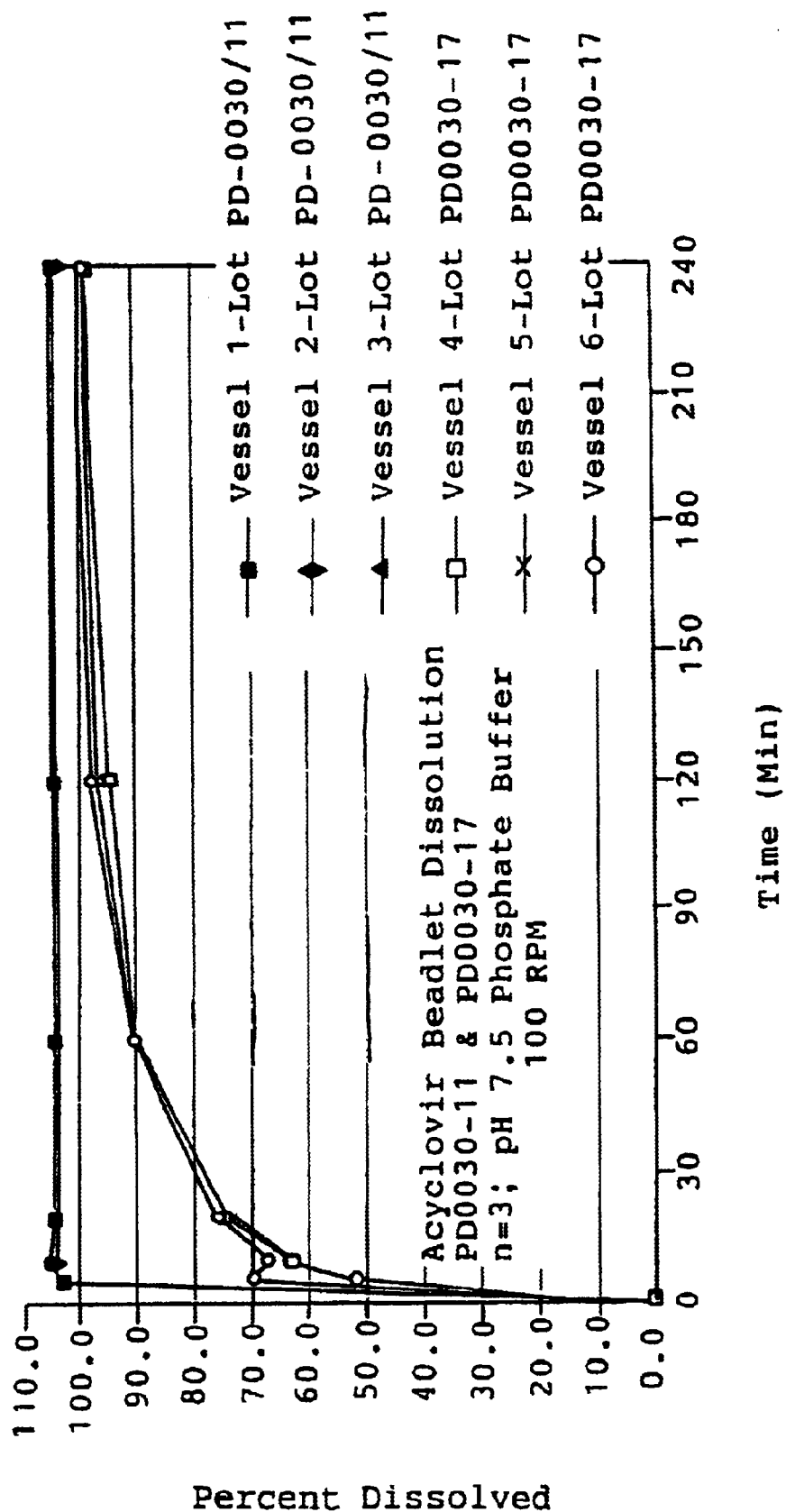
FIG. 3 is a plot of acyclovir-containing beadlet percent dissolution over time for two of the Formulations from Example 1. It illustrates the effect of different methods of preparing acyclovir-beadlets, i.e. spray-melt and spray congealing on acyclovir release.

FIG. 3 is a plot of acyclovir-containing beadlet percent dissolution over time for two of the Formulations from this Example (PD0030-11 and PD0030-17). It illustrates the effect of different methods of preparing acyclovir-beadlets, i.e. spray-melt and spray congealing on acyclovir release.

EXAMPLE 2

Coated and Uncoated Beadlet Formulations

Additional Formulations for coated and uncoated beadlets are provided in this Example. Preparation was as described above and in Tables 5 and 6.

TABLE 5

Coated And Uncoated Beadlet Formulations

| Formulation | PD0030-40A | PD0030-45 | PD0030-47 | PD0030-49 |
|---|---|---|---|---|
| Core Formulation | PD0030-14 | | | |
| Acyclovir (30 μm) | | | 25 | |
| Acyclovir (16 μm) | | 35 | | 25 |
| Labrasol | | 20 | 20 | 20 |
| Tween 20 | | | | |
| Compritol 888 ATO | | 40 | 55 | 54 |
| SLS | | | | |
| Citric Acid | | | | 1 |
| Talc | | 5 | | |
| Total | | 100 | 100 | 100 |
| Core Preparation | Hot-melt | Spray-melt Top spray | Spray-congeal Size >100 μm | Spray-congeal Top Spray |
| Blend pre-coat | | 10% Talc | 10% HPMCAS* | |
| Coating Method | Wurster | Wurster | Wurster | |
| Coating polymer | 8% Opadry | 20% 4110D** | 20% L30D | |
| Coating level | 5% | <2% | 10% | |

*HPMCAS = hydroxypropylmethylcellulose acetate succinate
**Eudragit 411 OD, a new enteric polymer

TABLE 6

Additional Coated Beadlet Formulations

| Formulation | PD0030-52 | PD0030-54 | PD0030-55 | PD0030-61 | PD0030-63 |
|---|---|---|---|---|---|
| Core Formulation | | | PD0030-47 | | |
| Acyclovir (Avg 30 μm) | | | | 35 | 0 |
| Acyclovir (Avg: 16 μm) | 30 | 30 | | | |
| Labrasol | 20 | 20 | | 20 | 20 |
| Compritol 888 ATO | 48 | 48 | | 40 | 58 |
| SLS | 1 | 1 | | | 1 |
| Citric Acid | 1 | 1 | | | 1 |
| Talc | — | — | | 5 | 20 |
| Total | 100 | 100 | | 100 | 100 |
| Core Preparation | Spray-melt Wurster | Hot-melt Wurster | | Spray-melt | Hot-melt Size<100μ |
| Blend pre-coat | | | 10% HPMCAS | | |
| Coating Method | | | Wurster | Wurster | |
| Coating polymer | | | 20% L30D | 20% L 30D | |
| Coating level | | | 50% | <2% | |

PD0030-52 and PD0030-54 illustrate beadlets made in a fluid bed processor with a Wurster inserter, used for either a spray-melt or a hot-melt granulation method. PD0030-47 and PD0030-55 illustrate that spray-congealed beadlets can be coated with an enteric polymer (Eudragit L30D) at a 10% coating level and a 50% coating level, respectively. PD0030-63 is a placebo formulation.

Beadlets having Formulations reported in this Example were tested for drug transport in the Caco-2 cell monolayer model described above. The results are reported in Table 7 and also in FIGS. 4 and 5.

TABLE 7

Acyclovir Transport Through Caco-2 Cell Monolayer

| Formulation | Initial Conc. (mg/ml) | Transport μg/ml/hr | Transport sample/control ratio |
|---|---|---|---|
| CONTROL | 33.3 | 44.2 | 1.0 |
| PD0030-49 | 33.3 | 735 | 16.6 |
| PD0030-54 | 40.0 | 631 | 14.3 |
| PD0030-63 | 00.0 | 0.319 | 0.0072 |
| CONTROL | 33.3 | 37.2 | 1.0 |
| PD0030-40A | 40.0 | 584 | 15.7 |
| PD0030-52 | 40.0 | 624 | 16.8 |
| PD0030-54 | 40.0 | 599 | 16.1 |
| PD0030-55 | 24.0 | 214 | 5.8 |

Figure 4:
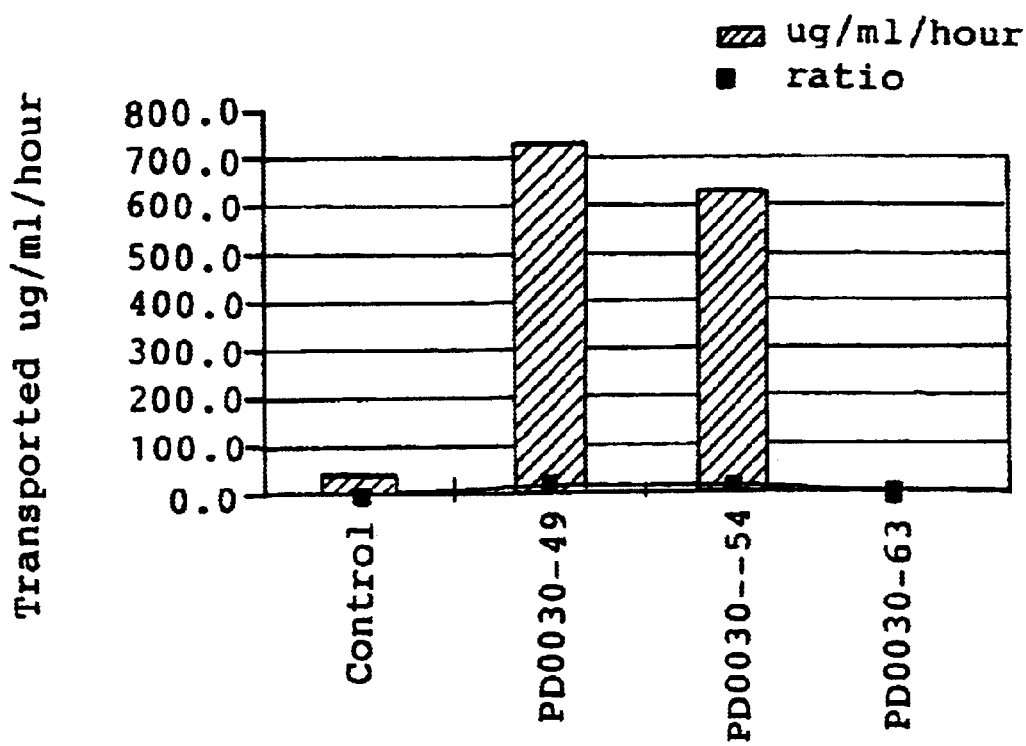
FIG. 4 is a plot of acyclovir transport through a Caco-2 cell monolayer using Formulations of Example 2. Spray congealed acyclovir-containing beadlets are compared with control and placebo.

FIG. 4 is a plot of acyclovir transport through a Caco-2 cell monolayer using Formulations of this Example. Spray congealed acyclovir-containing beadlets are compared with control and placebo.

Figure 5:
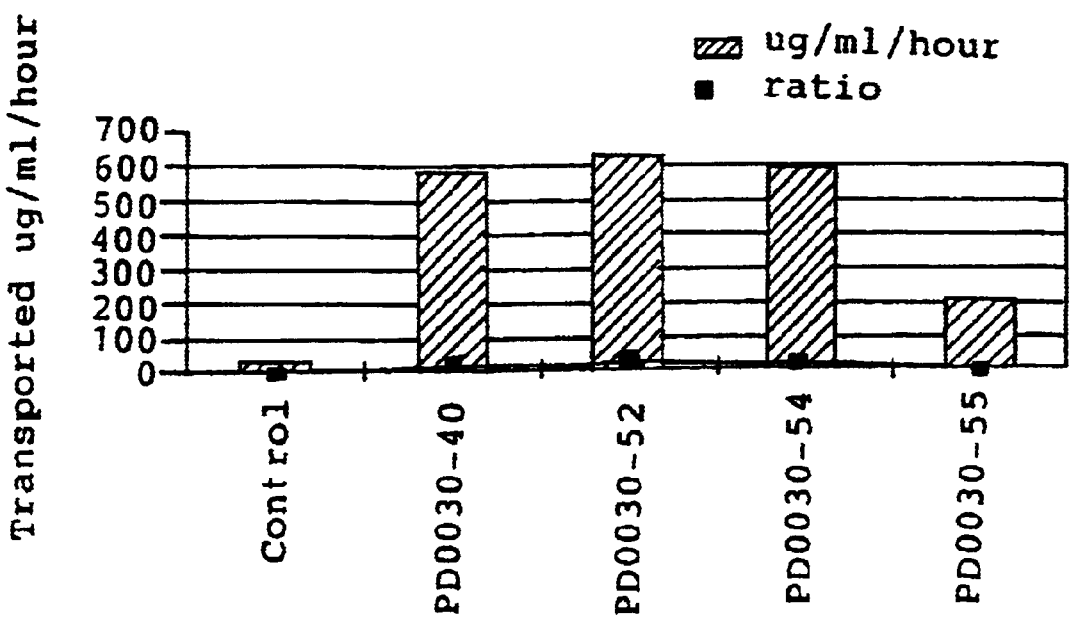
FIG. 5 is a plot of acyclovir transport through a Caco-2 cell monolayer using Formulations of Example 2. Peptiscreen® results of acyclovir from beadlets made by a variety of processes are presented. Beadlets of Formulation PD0030-40 has an optional coating applied.

FIG. 5 is a plot of acyclovir transport through a Caco-2 cell monolayer using Formulations of this Example. Peptiscreen® results of acyclovir from beadlets made by a variety of processes are presented. Beadlets of Formulation PD0030-40 have an optional coating applied.

Figure 6:
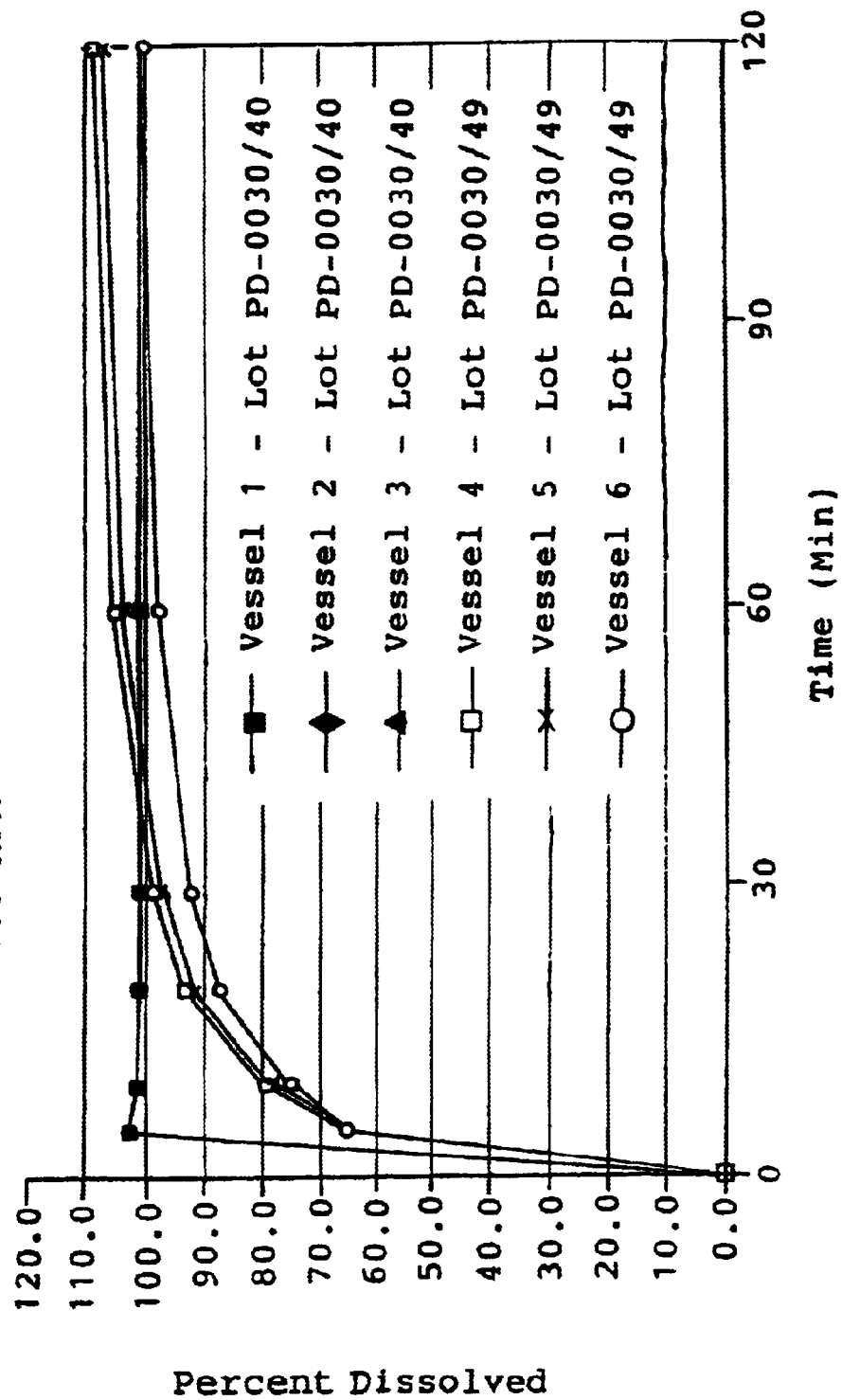
FIG. 6 is a plot of acyclovir-containing beadlet percent dissolution over time for two of the Formulations from Example 2. It illustrates dissolution results from coated acyclovir beadlets (Formulation PD0030-40) made by a hot melt granulation process and uncoated acyclovir beadlets (Formulation PD0030-49) made by a spray congealing method.

FIG. 6 is a plot of acyclovir-containing beadlet percent dissolution over time for two of the Formulations from this Example. It illustrates dissolution results from coated acyclovir beadlets (Formulation PD0030-40) made by a hot melt granulation process and uncoated acyclovir beadlets (Formulation PD0030-49) made by a spray congealing method.

Figure 7:
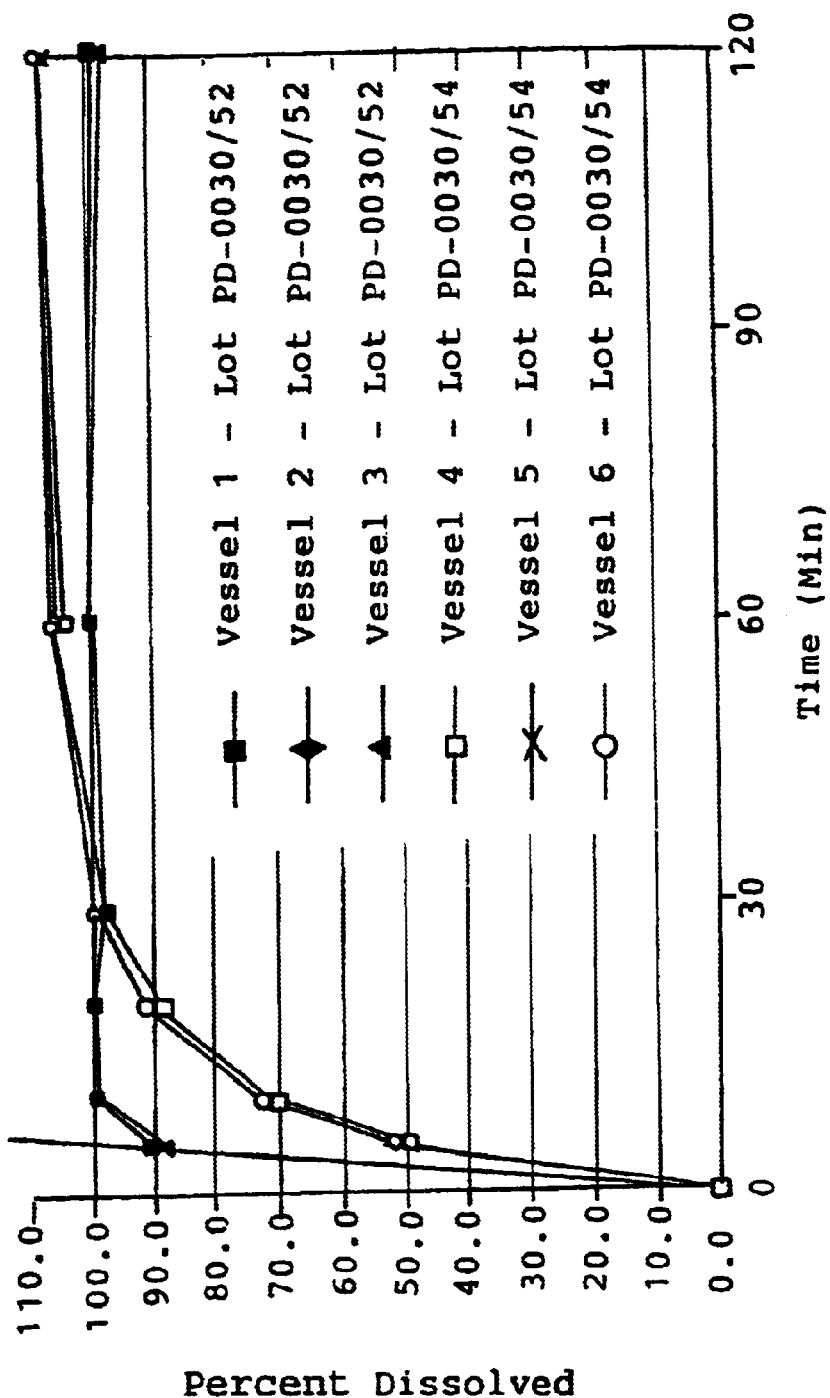
FIG. 7 is a plot of acyclovir-containing beadlet percent dissolution over time for two of the Formulations from Example 2. It illustrates dissolution results from acyclovir beadlets made by a spray melt process (Formulation PD0030-52) and a hot melt process (Formulation PD0030-54). Both procedures give immediate release beadlets containing 48% glyceryl behenate.

FIG. 7 is a plot of acyclovir-containing beadlet percent dissolution over time for two of the Formulations from this Example. It illustrates dissolution results from acyclovir beadlets made by a spray melt process (Formulation PD0030-52) and a hot melt process (Formulation PD0030-54). Both procedures give immediate release beadlets containing 48% glyceryl behenate.

EXAMPLE 3

Varied Manufacturing Procedures Give Uniform Transport Results

TABLE 8

Beadlet Formulations

| Formulation | PD0030-69 | PD0030-71 | PD0030-73 | PD0030-75 |
|---|---|---|---|---|
| Core Formulation | | | | |
| Acyclovir (Avg: 16 μm) | 30 | 30 | 30 | 30 |
| Labrasol | 20 | 20 | 20 | 20 |
| Compritol 888 ATO | 43 | 43 | 43 | 43 |
| SLS | 1 | 1 | 1 | 1 |
| Citric Acid | 1 | 1 | 1 | 1 |
| Talc | 5 | 5 | 5 | 5 |
| Total | 100 | 100 | 100 | 100 |
| Core Preparation | Hot-melt | Hot-melt | Hot-melt | Hot-melt |
| Product Temp. °C. | Low | Low | High | Low |
| Spray rate, g/min | High | Low | Low | Low |
| Melt and air temp., °C. | High | Low | High | High |

Figure 8:
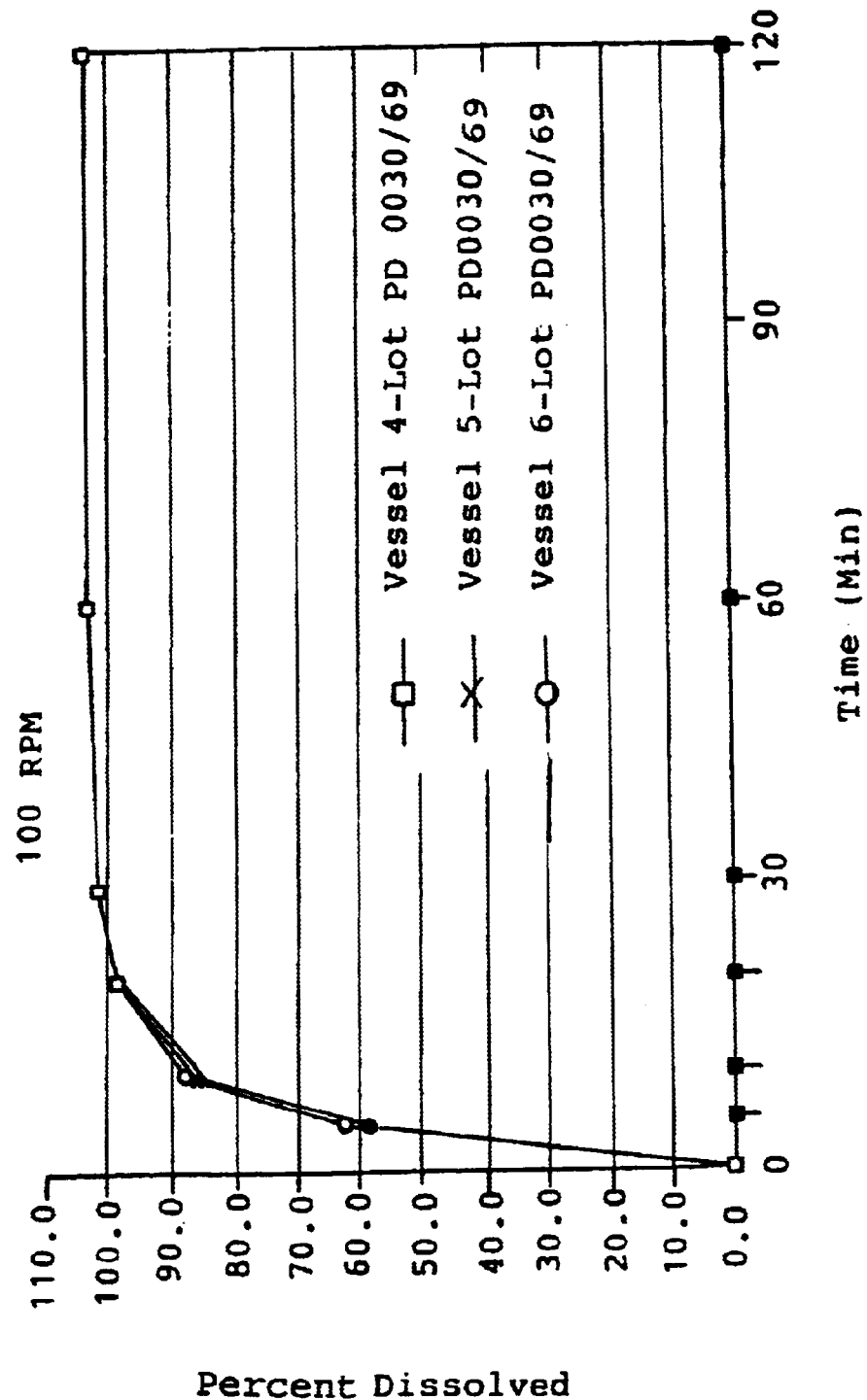
FIG. 8 is a plot of acyclovir-containing beadlet percent dissolution over time for one of the Formulations of Example 3.

FIG. 8 is a plot of acyclovir-containing beadlet percent dissolution over time for one of the Formulations of this Example (Formulation PD0030-69).

TABLE 9

Beadlet Formulations

| Formulation | PD0030-77 | PD0030-79 | PD0030-81 | PD0030-83 |
|---|---|---|---|---|
| Core Ingredients | | | | |
| Acyclovir (Avg: 16 μm) | 30 | 30 | 30 | 30 |
| Labrasol | 20 | 20 | 20 | 20 |
| Compritol 888 ATO | 43 | 43 | 43 | 43 |
| SLS | 1 | 1 | 1 | 1 |
| Citric Acid | 1 | 1 | 1 | 1 |
| Talc | 5 | 5 | 5 | 5 |
| Total | 100 | 100 | 100 | 100 |
| Core Preparation | Hot-melt | Hot-melt | Hot-melt | Hot-melt |
| Product Temp., °C. | High | Low | High | High |
| Spray rate, g/min | High | High | Low | High |
| Melt and air temp. °C. | High | Low | Low | Low |

TABLE 10

Acyclovir Formulations

| Formulation | PD0030-85 | PD0030-88 | PD0030-90 |
|---|---|---|---|
| Core Ingredients | | | PD0030-31 |
| Acyclovir (Avg: 16 μm) | 30 | — | 30 |
| Acyclovir (Avg: 30 μm) | — | 25 | — |
| Labrasol | — | — | 20 |
| Tween 20 | 20 | 20 | — |
| Compritol 888 ATO | 43 | 53 | 43 |
| SLS | 1 | 1 | 1 |

TABLE 10-continued

Acyclovir Formulations

| Formulation | PD0030-85 | PD0030-88 | PD0030-90 |
|---|---|---|---|
| Citric Acid | 1 | 1 | 1 |
| Talc | 5 | — | 5 |
| Total | 100 | 100 | 100 |
| Core Preparation | Hot-melt Size<100 μm | Spray congeal Beadlet <100 μm | Hot-melt |
| Coating Method | | | Top |
| Coating polymer | | | 10% Opadry |
| Coating level | | | 10% |

PD0030-90 illustrates that beadlets can be coated with a Opadry® polymer solution using a conventional fluid bed processor.

TABLE 11

Beadlet Formulations

| Formulation | PD0030-98 | PD0033-04 |
|---|---|---|
| Core Formulation | PD0030-85 | PD0030-88 |
| Core Preparation | Hot-melt | Spray-congeal |
| Coating Method | Wurster | Wurster |
| Coating polymer | 10% Opadry | 8% Opadry |
| Coating level | 20% | 20% |

Table 11 shows that Acyclovir beadlets can be coated with opadry polymer individually, regardless of preparation methods, e.g., hot-melt or spray-congealing.

Beadlets having Formulations reported in this Example were tested for drug transport in the Caco-2 cell monolayer model described above. The results are reported in Table 12 and also in FIG. 9.

TABLE 12

Acyclovir Transport Through Caco-2 Cell Monolayers

| Formulation | Initial Conc. (mg/ml) | Transport ug/ml/hr | Transport sample/control ratio |
|---|---|---|---|
| Control | 33.3 | 27.7 | 1.0 |
| PD0030-69 | 40.0 | 989 | 35.7 |
| PD0030-71 | 40.0 | 1050 | 38.0 |
| PD0030-85 | 40.0 | 1138 | 41.1 |
| PD0030-88 | 33.3 | 1184 | 42.8 |
| PD0030-90 | 13.3 | 1016 | 36.7 |
| PD0030-98 | 26.7 | 1007 | 36.4 |
| PD0033-04 | 20.0 | 1063 | 38.4 |

Figure 9:
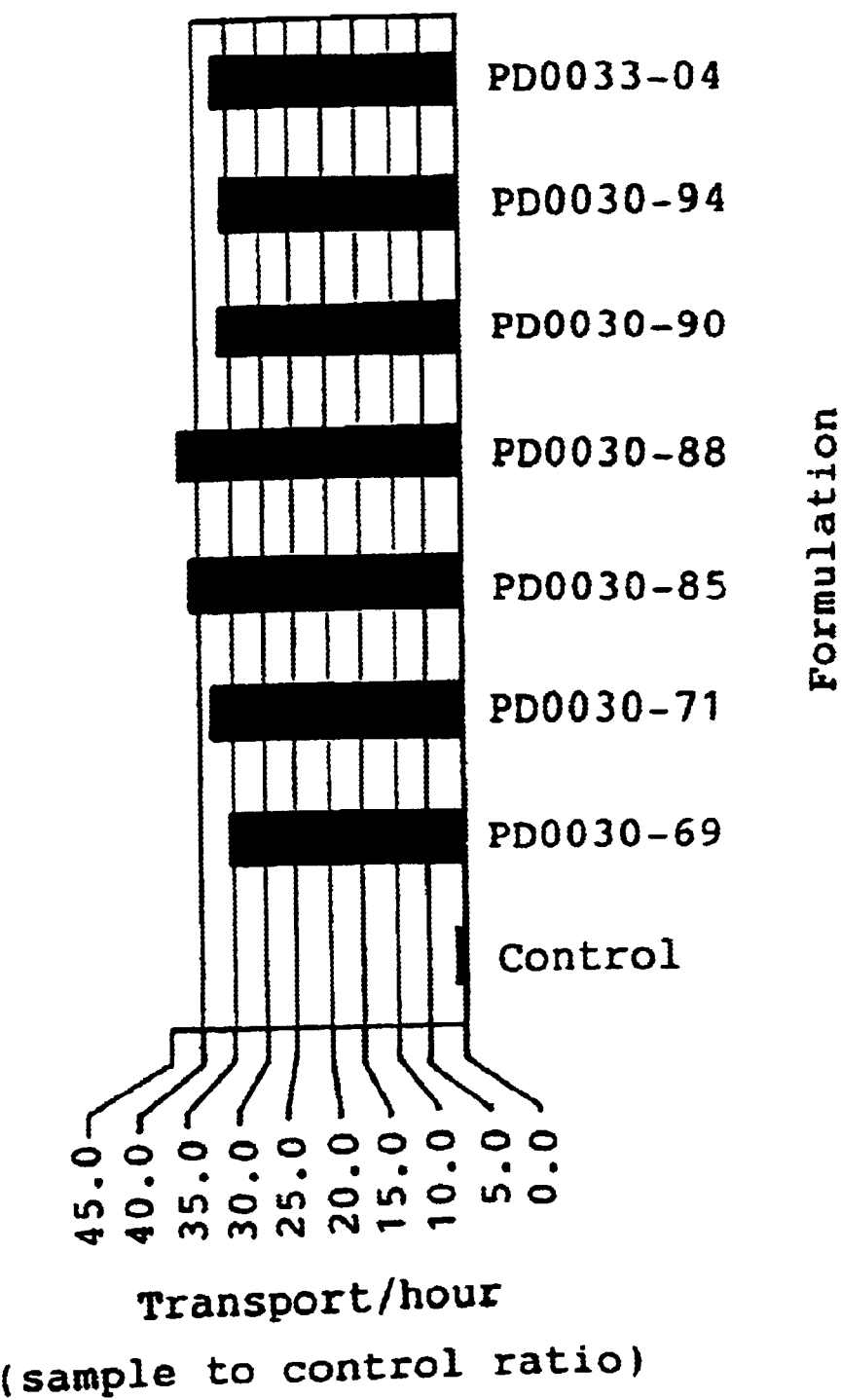
FIG. 9 is a plot of acyclovir transport through a Caco-2 cell monolayer using several of the Formulations described in Example 3. Peptiscreen® results of acyclovir transport from beadlets made by either spray congealing or hot melt granulation containing an anti-attacking agent are presented. Coated and uncoated beadlets are compared to the control.

FIG. 9 is a plot of acyclovir transport through a Caco-2 cell monolayer using several of the Formulations described in this Example. Peptiscreen® results of acyclovir transport from beadlets made by either spray congealing or hot melt granulation containing an anti-attacking agent are presented. Coated and uncoated beadlets are compared to the control.

Figure 10:
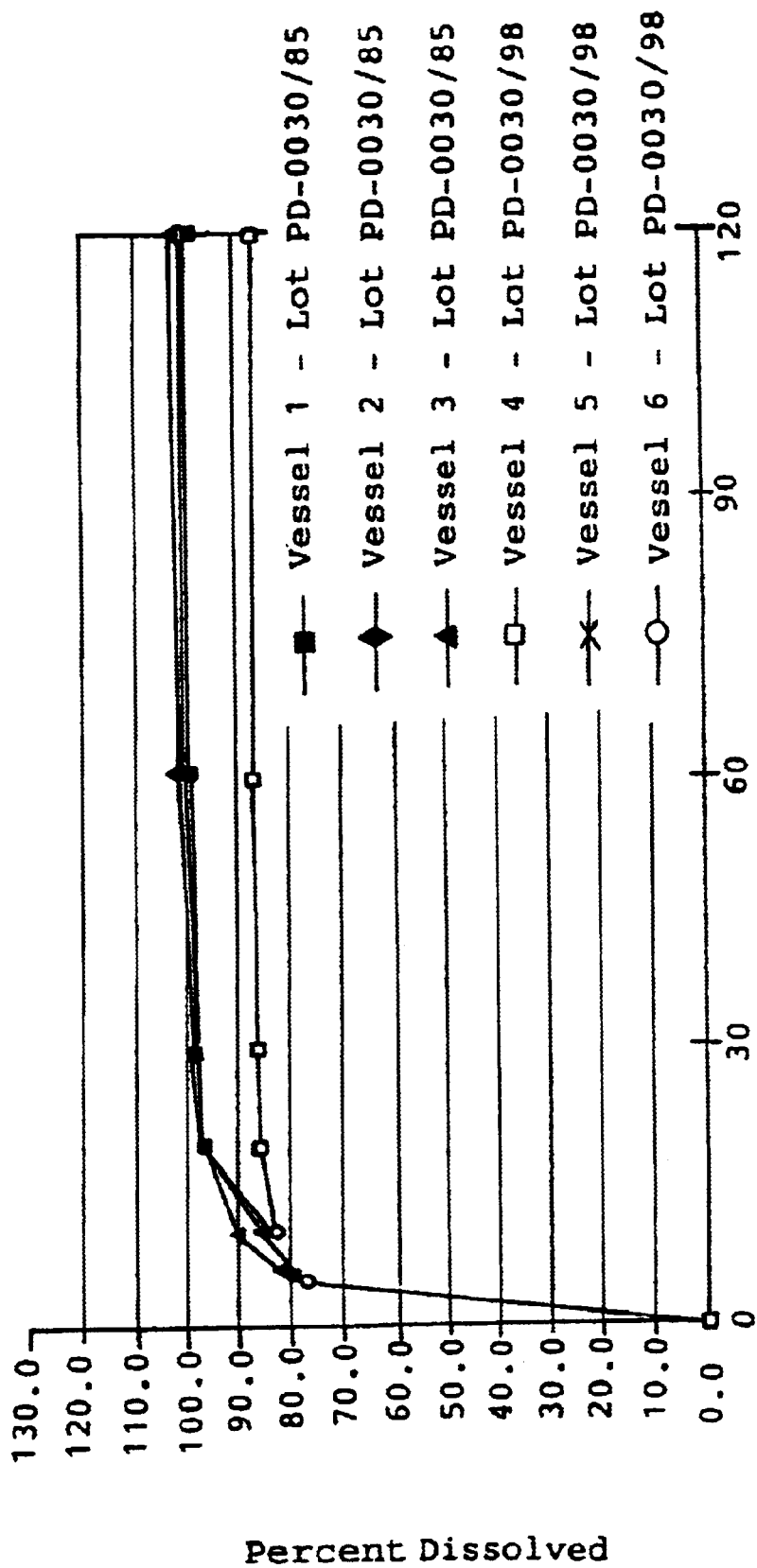
FIG. 10 is a plot of acyclovir-containing beadlet percent dissolutions over time for two of the Formulations from Example 3. It illustrates dissolution of acyclovir-containing hot melt beadlets, comparing Opadry coated beadlets with uncoated beadlets.

FIG. 10 is a plot of acyclovir-containing beadlet percent dissolutions over time for two of the Formulations from this Example. It illustrates dissolution of acyclovir-containing hot melt beadlets, comparing Opadry® coated beadlets with uncoated beadlets.

EXAMPLE 4

Tablets Formed Using Various Beadlet Formulations

TABLE 13

Tablet Formulations

| Formulation | PD0029-39 | PD0029-40 | PD0029-41A | PD0029-41B |
|---|---|---|---|---|
| Tablet Formulation | | | | |
| Acyclovir Granules | 50 | 50 | 50 | 50 |
| Core Formulation | PD0030-85 | PD0030-90 | PD0030-90 | PD0030-90 |
| Avicel PH302 | 38 | 38 | 43 | 46 |
| Ac-Di-Sol | 10 | 10 | 5 | 2 |
| Cab-O-Sil | 1 | 1 | 1 | 1 |
| SLS | 1 | 1 | 1 | 1 |
| Note | Stokes | Stokes | Stokes | Stokes |
| Tablet wt., mg | 400 | 440 | 440 | 440 |
| Shape | round | round | round | round |
| Hardness, Kp | N/A | 5 | 5 | 6 |

TABLE 14

Tablet Formulations

| Formulation | PD0029-41C | PD0029-43A | PD0029-43B | PD0029-43C |
|---|---|---|---|---|
| Tablet Formulation | | | | |
| Acyclovir Granules | 50 | 50 | 60 | 70 |
| Core Formulation | PD0030-90 | PD0030-90 | PD0030-90 | PD0030-90 |
| Avicel PH302 | 48 | 45 | 35 | 25 |
| Lactose 316 | — | — | — | 8 |
| Ac-Di-Sol | — | 3 | 3 | 3 |
| Cab-O-Sil | 1 | 1 | 1 | 1 |
| SLS | 1 | — | — | — |
| Mg Stearate | — | 1 | 1 | 1 |
| Note | Stokes | Stokes | Stokes | Stokes |
| Tablet wt., mg | 440 | 400 | 400 | 400 |
| Shape | round | round | round | round |
| Hardness, Kp | 6–6.5 | 5 | 5 | 5 |

These tablets were made to demonstrate that beadlet tablets could be made with water soluble lubricants (Formulations PD0029-39 and PD0029-40) and to study the effect of a disintegration agent on drug release from tablets (Formulations PD0029-40 and PD0029-41AC). Also, the amount of acyclovir granules was varied to examine the effect on drug release from the tablets.

Formulations PD0029-44A and -44B illustrate the addition of lubricant to tablet preparations. The tablets were studied for the effect of this on drug release.

Formulations PD0029-45A through -45C illustrate the addition of starch 1500 to tablet preparations. The tablets were studied for the effect of this on drug release.

TABLE 16

Beadlet Tablet Formulations

| Formulation | PD0033-07A | PD0033-07B | PD0033-07C | PD0033-09A |
|---|---|---|---|---|
| Core Formulation | | | | |
| Acyclovir, USP | 61.0 | 54.3 | 50 | 61.0 |
| Labrasol | 7.6 | 9.1 | 10 | 11.4 |
| Compritol 888 ATO | 29.0 | 34.4 | 38 | 25.2 |
| SLS | 1.2 | 1.1 | 1 | 1.2 |
| Citric Acid | 1.2 | 1.1 | 1 | 1.2 |
| Total | 100 | 100 | 100 | 100 |
| Granulation Method | Hot-melt | Hot-melt | Hot-melt | Hot-melt |
| Product Temp., °C. | 40 | 40 | 40 | 40 |
| Spray rate, g/min | 60 | 60 | 60 | 60 |
| Melt and air temp., °C. | 120 | 120 | 120 | 120 |
| Bulk density, g/ml | | | 0.36 | |
| Tap density, g/ml | | | 0.57 | |
| % larger than 140 mesh | | | 6.1 | |
| Ave. particle size, μm | | | <100 μm | |

TABLE 15

Beadlet Tablet Formulations

| Formulation | PD0029-44A | PD0029-44B | PD0029-45A | PD0029-45B | PD0029-45C |
|---|---|---|---|---|---|
| Tablet Formulation | | | | | |
| Acyclovir Granules | 60 | 60 | 60 | 60 | 60 |
| Core Formulation | PD0030-90 | PD0030-90 | PD0030-90 | PD0030-90 | PD0030-90 |
| Avicel PH302 ATO | 36 | 34 | 30 | 25 | 20 |
| Starch 1500 | 0 | 0 | 5 | 10 | 15 |
| Ac-Di-Sol | 3 | 3 | 3 | 3 | 3 |
| Cab-O-Sil | 1 | 1 | 1 | 1 | 1 |
| Mg Stearate | 0 | 2 | 1 | 1 | 1 |
| Note | Stokes | Stokes | Stokes | Stokes | Stokes |
| Tablet wt., mg | 400 | 400 | 430 | 430 | 430 |
| Shape | round | round | round | round | round |
| Hardness, Kp | N/A | 5 | 6 | 5 | 4.6 |

TABLE 17

Beadlet Tablet Formulations

| Formulation | PD0033-09B | PD0033-09C | PD0033-11A | PD0033-11B | PD0033-11C |
|---|---|---|---|---|---|
| Core Formulation | | | | | |
| Acyclovir, USP | 57.7 | 50 | 63.4 | 57.7 | 50 |
| Labrasol | 12.5 | 15 | 12.5 | 16.7 | 20 |
| Compritol 888 ATO | 27.5 | 33 | 17.5 | 23.3 | 28 |
| SLS | 1.15 | 1 | 1.3 | 1.15 | 1 |
| Citric Acid | 1.15 | 1 | 1.3 | 1.15 | 1 |
| Total | 100 | 100 | 100 | 100 | 100 |
| Granulation Method | Hot-melt | Hot-melt | Hot-melt | Hot-melt | Hot-melt |
| Product Temp., °C. | 40 | 40 | 40 | 40 | 40 |
| Spray rate, g/min | 60 | 60 | 60 | 60 | 60 |
| Melt and air temp., °C. | 120 | 120 | 120 | 120 | 120 |
| Bulk density, g/ml | | 0.33 | | | 0.33 |
| Tap density, g/ml | | 0.54 | | | 0.55 |
| % larger than 140 mesh | | 16.2 | | | 26.2 |

In Tables 16 and 17, PD0033-07A through -07C, PD0033-09A through -09C and PD0033-11A through -11C were prepared to study the effect of transport enhancer on processing and drug transport a Caco 2 cell monolayer.

The Labrasol® content was also modified to cover the range from 7.6% to 20%.

TABLE 18

Beadlet Tablet Formulations

| Formulation | PD0033-13A | PD0033-13B | PD0033-13C | PD0033-15 |
|---|---|---|---|---|
| Core Formulation | | | | PD0033-13C |
| Acyclovir, USP | 61.0 | 54.3 | 50 | |
| Tween 20 | 11.4 | 13.6 | 15 | |
| Compritol 888 ATO | 25.2 | 29.9 | 33 | |
| SLS | 1.2 | 1.1 | 1 | |
| Citric Acid | 1.2 | 1.1 | 1 | |
| Total | 100 | 100 | 100 | |
| Granulation Method | Hot-melt | Hot-melt | Hot-melt | |
| Product Temp., °C. | 40 | 40 | 40 | |
| Spray rate, g/min | 60 | 60 | 60 | |
| Melt & air temp.,° C. | 120 | 120 | 120 | |
| Coating method | | | | Top spray |
| Coating polymer | | | | 15% Opadry-II |
| Coating level | | | | 10% |
| Note | | | | 1% Cabosil |
| Bulk density, g/ml | | | 0.35 | 0.29 |
| Tap density, g/ml | | | 0.54 | 0.38 |

In Table 18, PD33-13A through -13C show different amounts of transport enhancers to study their effect on processing and drug transport.

Formulation PD0033-15 shows coating of a beadlet formed by hot-melt granulation with Opadry® II.

TABLE 19

Acyclovir Transport Through Caco-2 Cell Monolayers

| Formulation | Initial Conc. (mg/ml) | Transport ug/ml/hr | Transport sample/control ratio |
|---|---|---|---|
| CONTROL | 66.6 | 18.9 | 1.0 |
| PD0033-07A | 66.6 | 786 | 41.5 |
| PD0033-07B | 66.6 | 817 | 43.2 |
| PD0033-07C | 66.6 | 805 | 52.5 |
| PD0033-09A | 66.6 | 899 | 47.5 |
| PD0033-09B | 66.6 | 891 | 47.1 |
| PD0033-09C | 66.6 | 898 | 47.5 |
| PD0033-11A | 66.6 | 930 | 49.2 |
| PD0033-11B | 66.6 | 967 | 51.1 |
| PD0033-11C | 66.6 | 994 | 52.5 |
| PD0033-13A | 66.6 | 1127 | 59.6 |
| PD0033-13B | 66.6 | 1119 | 59.1 |
| PD0033-13C | 66.6 | 1056 | 55.8 |

Figure 11:
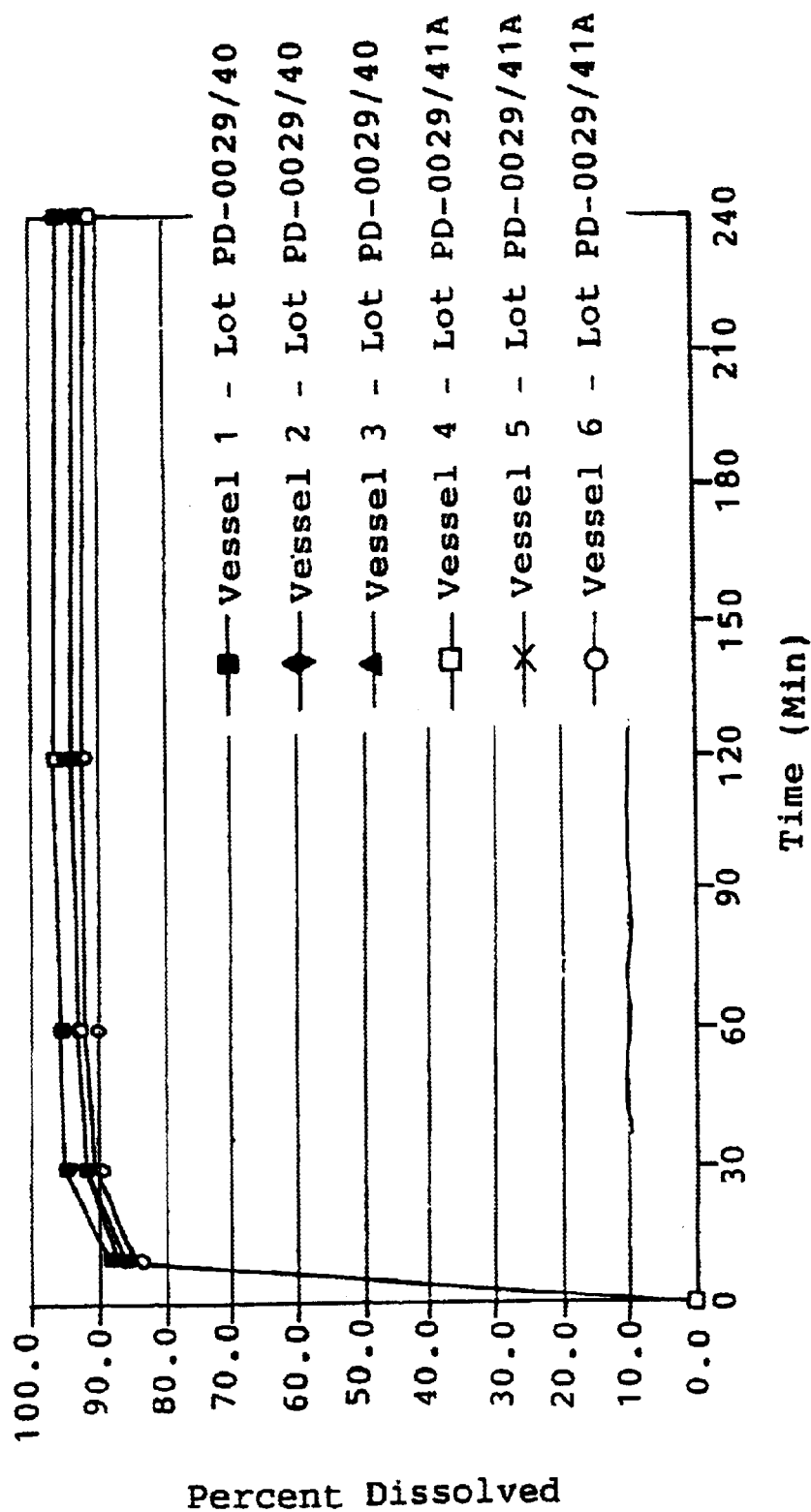
FIG. 11 is a plot of acyclovir-containing tablet percent dissolution over time for two of the Formulations from Example 4. It illustrates dissolution results from acyclovir tablets containing coated beadlets made by the hot melt granulation process.

FIG. 11 is a plot of acyclovir-containing tablet percent dissolution over time for two of the Formulations from this Example. It illustrates dissolution results from acyclovir tablets containing coated beadlets made by the hot melt granulation process.

Figure 12:
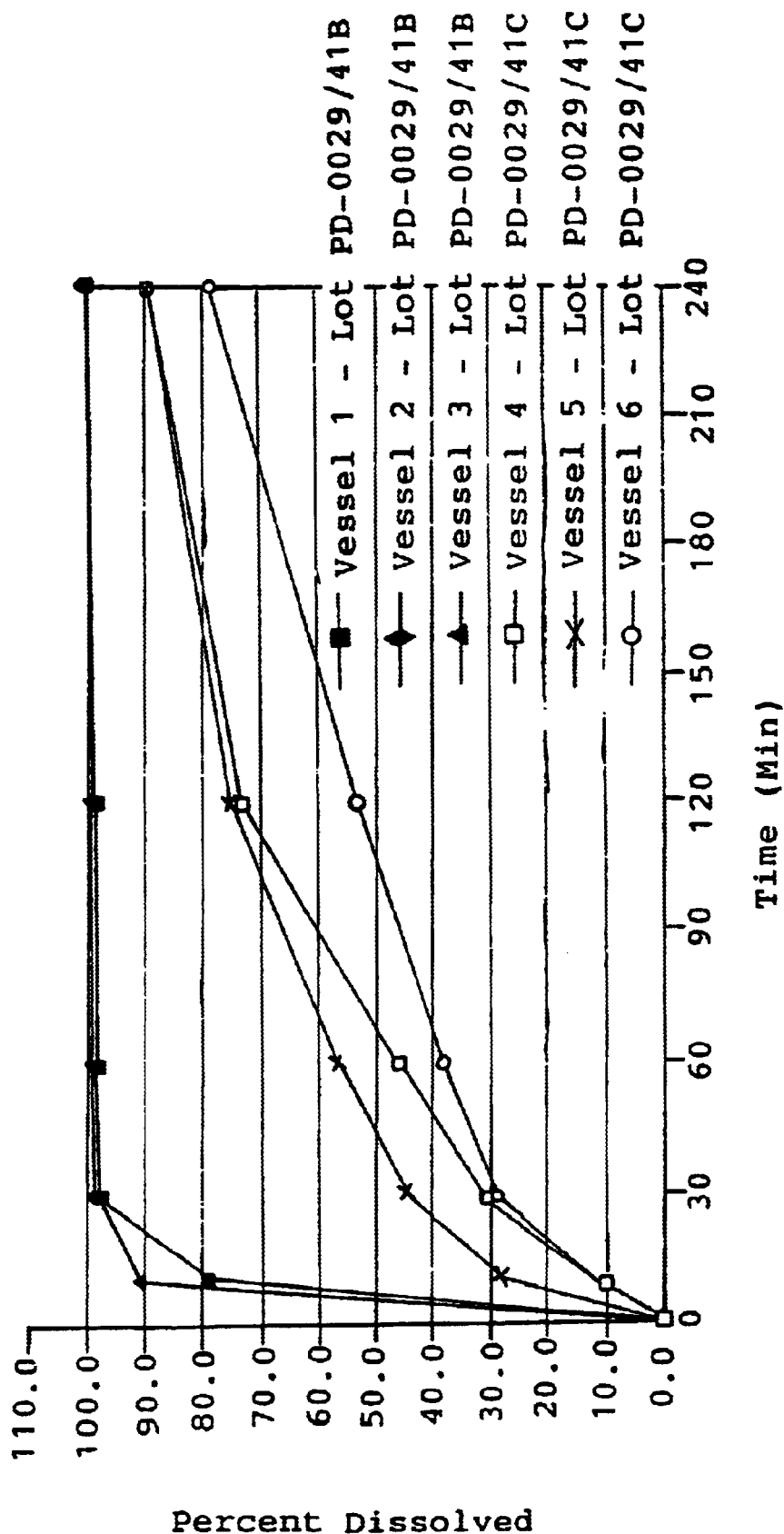
FIG. 12 is a plot of acyclovir-containing tablet percent dissolution over time for two of the Formulations from Example 4. It illustrates the difference between tablets that contain Ac-Di-Sol® (Formulation PD0029-41B) and those that do not contain Ac-Di-Sol® (Formulation PD0029-41C) a rapid disintegrant.

FIG. 12 is a plot of acyclovir-containing tablet percent dissolution over time for two of the Formulations from this Example. It illustrates the difference between tablets that contain Ac-Di-Sol® (Formulation PD0029-41B) and those that do not contain Ac-Di-Sol® (Formulation PD0029-41C) a rapid disintegrant.

Figure 13:
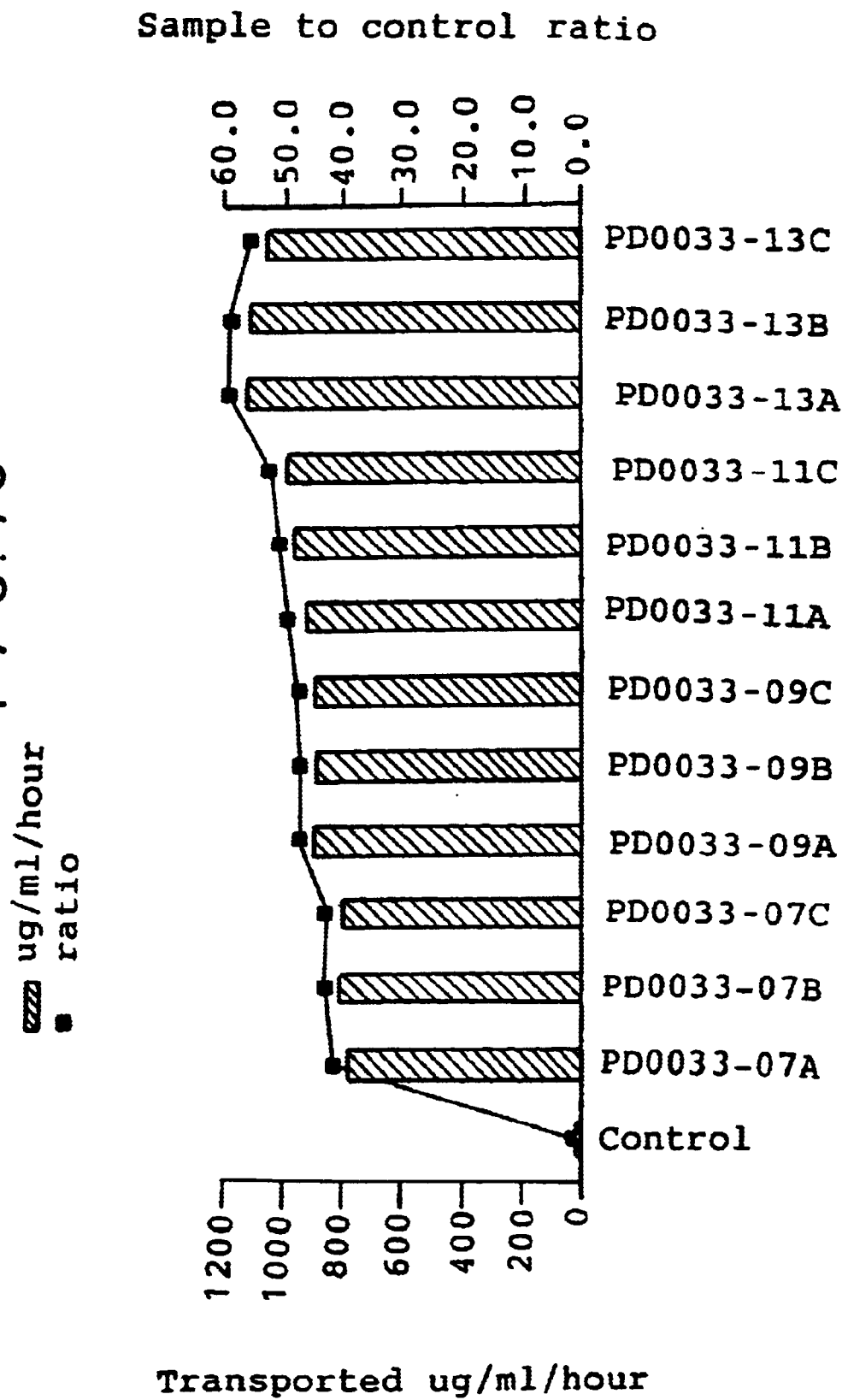
FIG. 13 is a plot of acyclovir transport through a Caco-2 cell monolayer using several formulations from Example 4. Peptiscreen® results of acyclovir transport from beadlets made by hot-melt granulation containing various percentages of Compritol 888 ATO and acyclovir are presented.

Beadlets having Formulations reported in this Example were tested for drug transport in the Caco-2 cell monolayer model described above. FIG. 13 is a plot of acyclovir transport through a Caco-2 cell monolayer using several formulations from this Example. Peptiscreen® results of acyclovir transport from beadlets made by hot-melt granulation containing various percentages of Compritol 888 ATO and acyclovir are presented. The data are in tabular form in Table 19.

EXAMPLE 5

TABLE 20

Beadlet Tablet Formulations

| Formulation | PD0029-54A | PD0029-54B | PD0029-54C | PD0029-55A |
|---|---|---|---|---|
| Tablet Formulation | | | | |
| Acyclovir granules | 50 | 50 | 50 | 50 |
| Core Formulation | PD0033-07C | PD0033-09C | PD0033-13C | PD0033-13C |
| Avicel PH 302 | 24 | 24 | 24 | 36 |
| Starch 1500 | — | — | — | 10 |
| Caistar | 14 | 14 | 14 | — |
| AC-Di-Sol | 2 | 2 | 2 | 2 |
| Talc | 5 | 5 | 5 | — |
| Cab-O-Sil | 1 | 1 | 1 | 0.5 |
| SLS | 1 | 1 | 1 | 1 |
| Na Stearoyl Fumarate | 3 | 3 | 3 | — |
| Mg Stearate | — | — | — | 0.5 |
| Note | Stokes | Stokes | Stokes | Stokes |
| Tablet wt., mg | 400 | 400 | 400 | 400 |
| Shape | round | round | round | round |
| Hardness, Kp | 5.5 | 5 | 5 | 5 |

Figure 14:
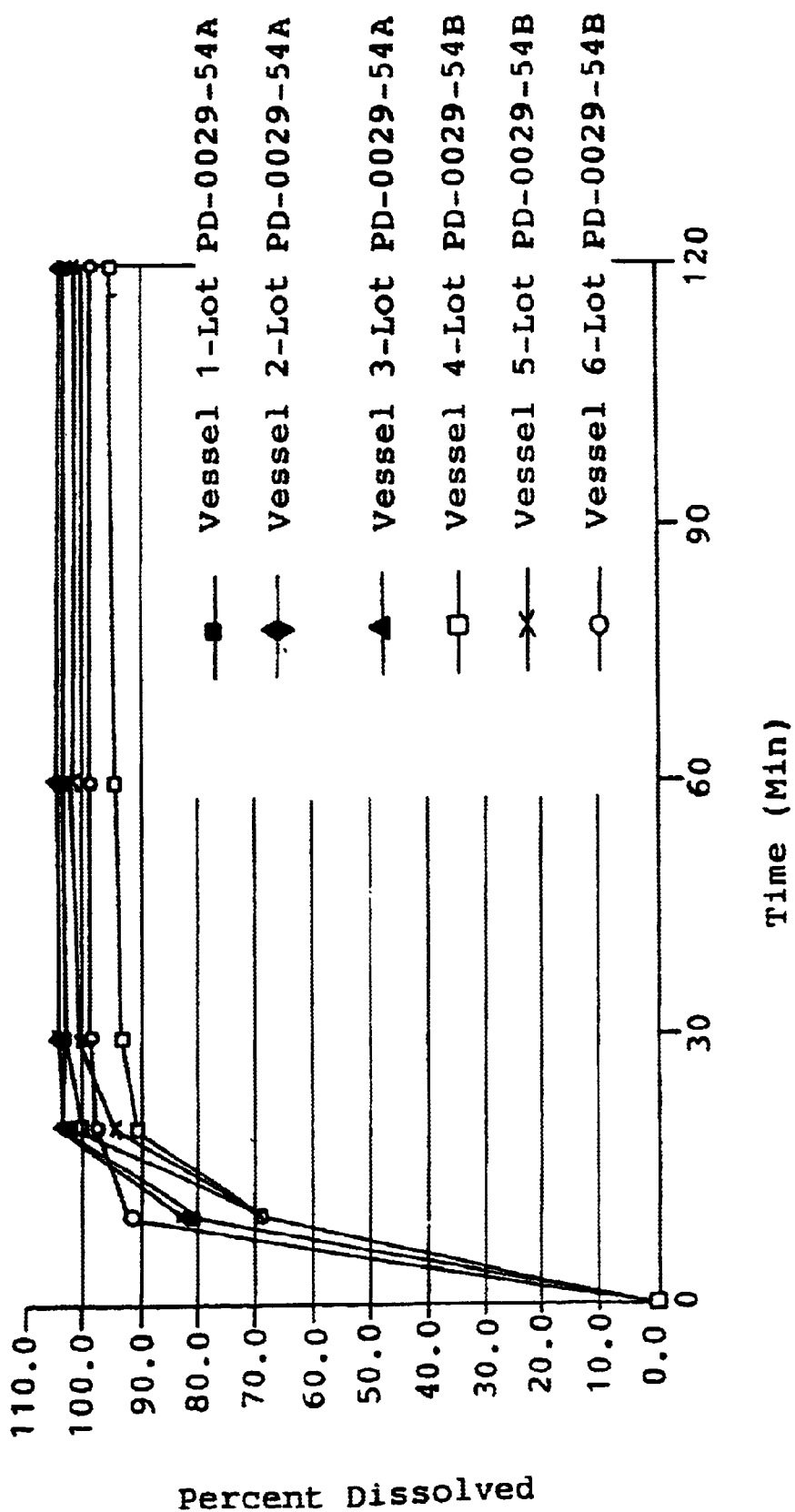
FIG. 14 is a plot of acyclovir-containing tablet percent dissolution over time for two of the Formulations from Example 5. These are 100 mg acyclovir tablets containing Labrasol® beadlets with an Opadry® coating.

FIG. 14 is a plot of acyclovir-containing tablet percent dissolution over time for two of the Formulations from this Example. These are 100 mg acyclovir tablets containing Labrasol® beadlets with an Opadry® coating.

Figure 15:
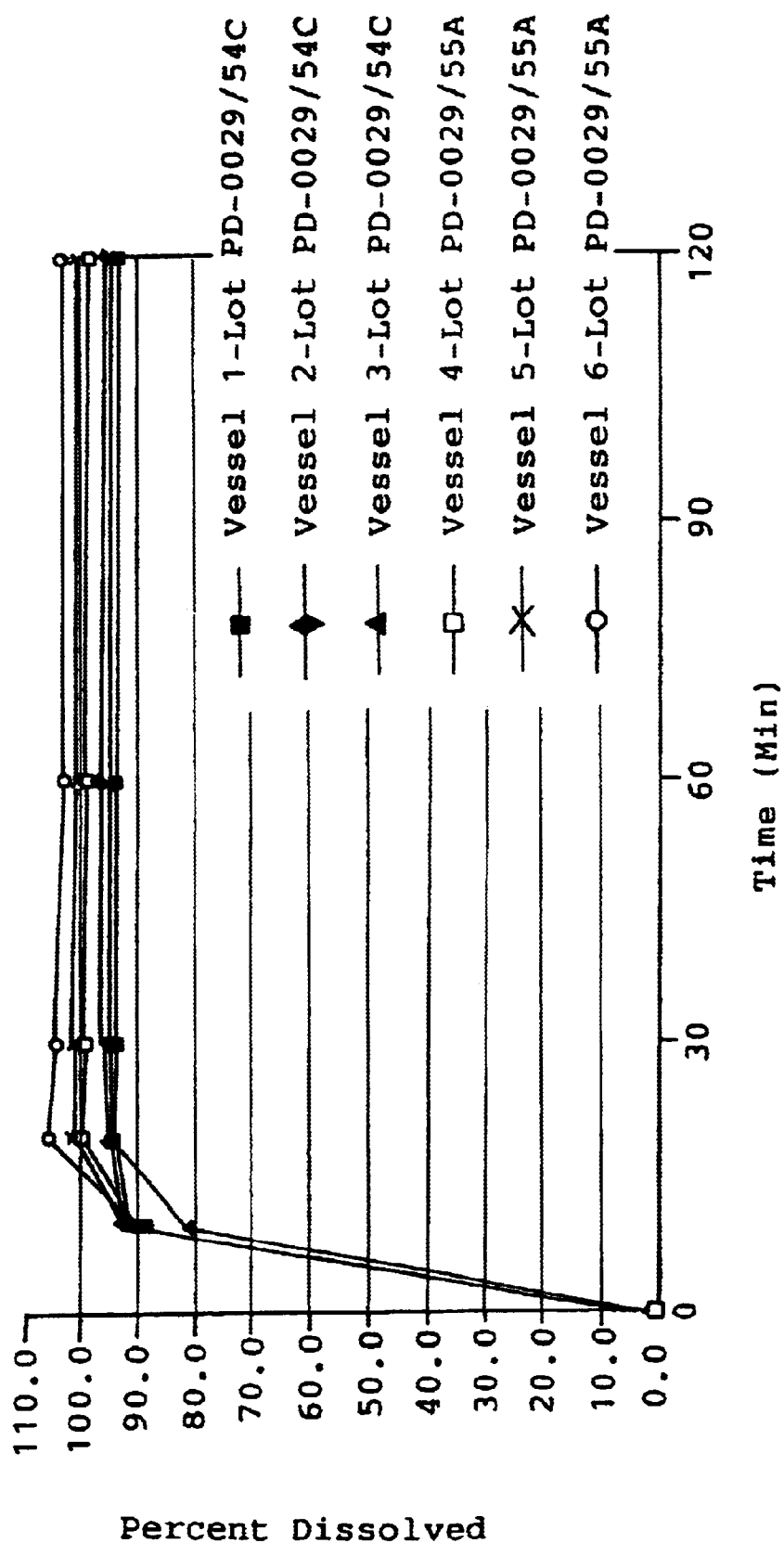
FIG. 15 is a plot of acyclovir-containing tablet percent dissolution over time for two of the Formulations from Example 5 containing different tabletting excipients.

FIG. 15 is a plot of acyclovir-containing tablet percent dissolution over time for two of the Formulations from this Example containing different tabletting excipients.

TABLE 21

Acyclovir Tablet Formulations

| Formulation | PD0029-55B | PD0029-55C | PD0029-55D | PD0029-56A |
|---|---|---|---|---|
| | | | | 15% opadry |
| Tablet Formulation | | | | |
| Acyclovir granules | 50 | 50 | 50 | 50 |
| Core Formulation | PD0033-13C | PD0033-17 | PD0033-17 | PD0033-17 |
| Avicel PH 102 | | 34 | 34 | 33 |
| Starch 1500 | 10 | 10 | 10 | 10 |
| AC-Di-Sol | 2 | 2 | 2 | 2 |
| Talc | | | 4 | |
| Cab-O-Sil | 0.5 | 0.5 | 0.5 | 0.5 |
| SLS | 1 | 1 | 1 | 1 |
| Na Stearoyl Fumarate | — | — | — | 6 |
| Mg Stearate | 0.5 | 0.5 | 0.5 | 0.5 |
| Myvaplex TL | — | 2 | — | 3 |
| Stearic Acid | | | 2 | |
| Note | Stokes | Stokes | Stokes | Stokes |
| Tablet wt., mg | 400 | 400 | 400 | 400 |
| Shape | round | round | round | round |
| Hardness, Kp | 5 | 5.4 | 5.2 | 5 |

Figure 16:
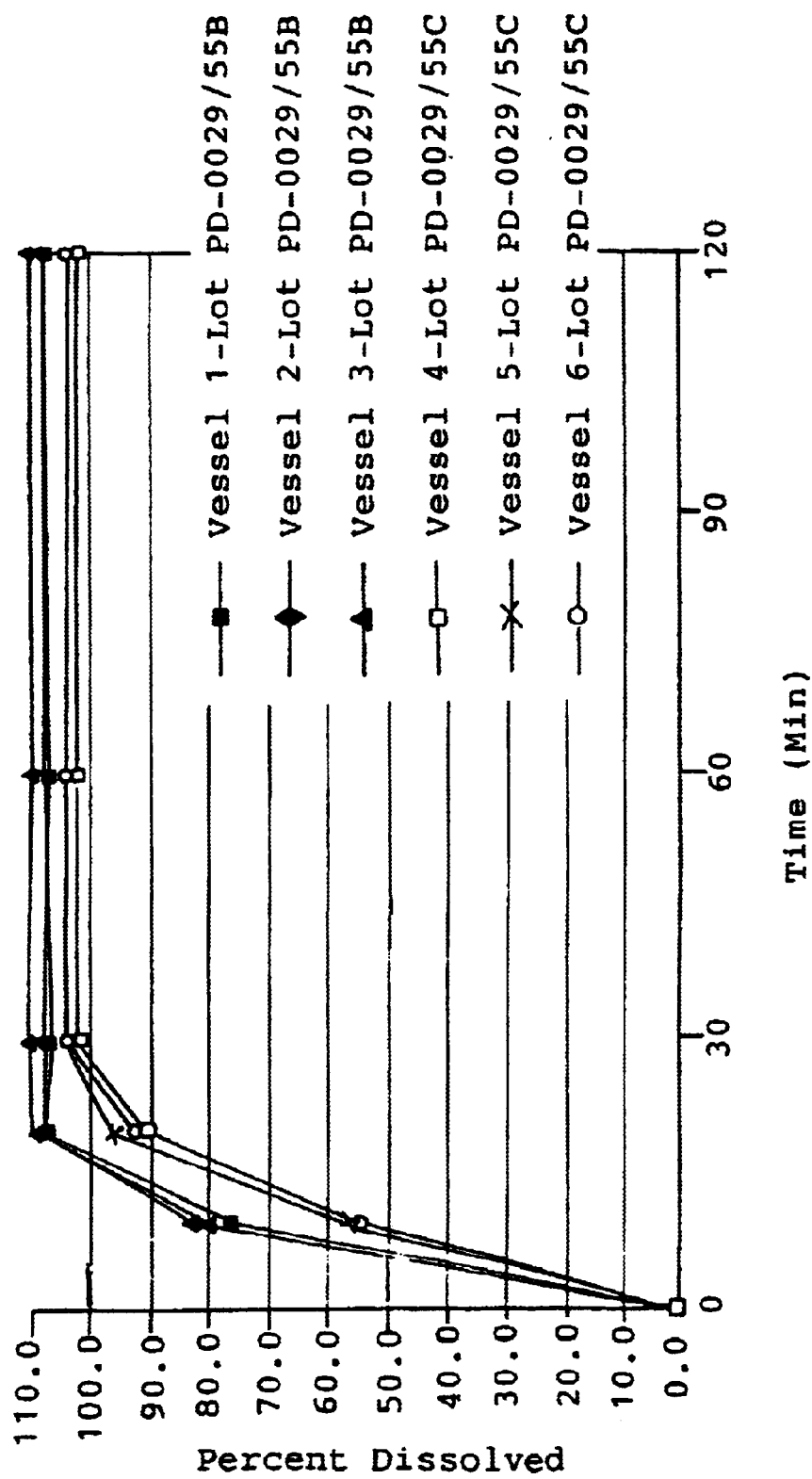
FIG. 16 is a plot of acyclovir-containing tablet percent dissolution over time for two of the Formulations from Example 5. It illustrates the effect of different tabletting excipients on dissolution of acyclovir tablets containing coated beadlets.

FIG. 16 is a plot of acyclovir-containing tablet percent dissolution over time for two of the Formulations from this Example. It illustrates the effect of different tabletting excipients on dissolution of acyclovir tablets containing coated beadlets. See Tables 20 and 21.

Figure 17:
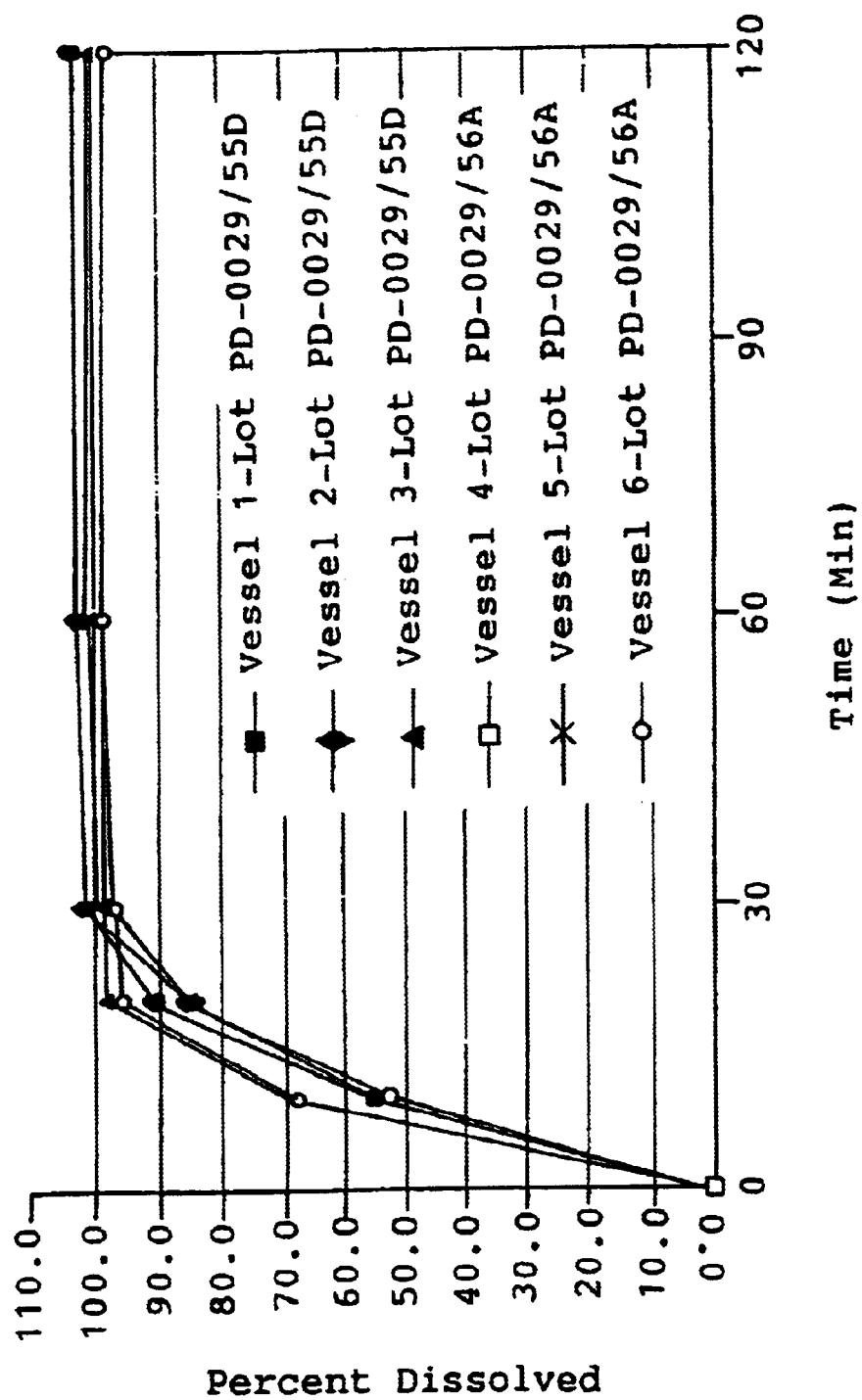
FIG. 17 is a plot of acyclovir-containing tablet percent dissolution over time for two of the Formulations from Example 5. It illustrates dissolution results from 100 mg acyclovir tablets containing coated beadlets blended with various tabletting lubricants.

FIG. 17 is a plot of acyclovir-containing tablet percent dissolution over time for two of the Formulations from this Example. It illustrates dissolution results from 100 mg acyclovir tablets containing coated beadlets blended with various tabletting lubricants. As much as 6% sodium stearoyl fumarate is used in Formulation PD0029-56A, with loss in immediate release properties. See Table 21.

EXAMPLE 6

Beadlet Coated Granulation Formulations

TABLE 22

Beadlet Formulations

| Formulation | PD0033-45 | PD0033-55 |
|---|---|---|
| | | 10% Opadry |
| Tablet Formulation | | |
| Acyclovir granules | 50 | 50 |
| Core Formulation | PD0033-38 | PD0033-40 |
| Avicel PH 301 | 34 | 31 |
| Lactose 316 | 10 | 10 |
| Starch 1500 | | |
| Calstar | | |
| AC-Di-Sol | 2 | 2 |
| Corn Starch | | |
| Cab-O-Sil | 0.5 | 0.5 |
| SLS | 1 | 1 |
| Stearic acid | 2 | 4 |
| Mg Stearate | 0.5 | 1.5 |
| Note | | Stokes |
| Tablet wt., mg | 400 | 400 |
| Shape | round | round |
| Hardness, Kp | | 6 |

Figure 18:
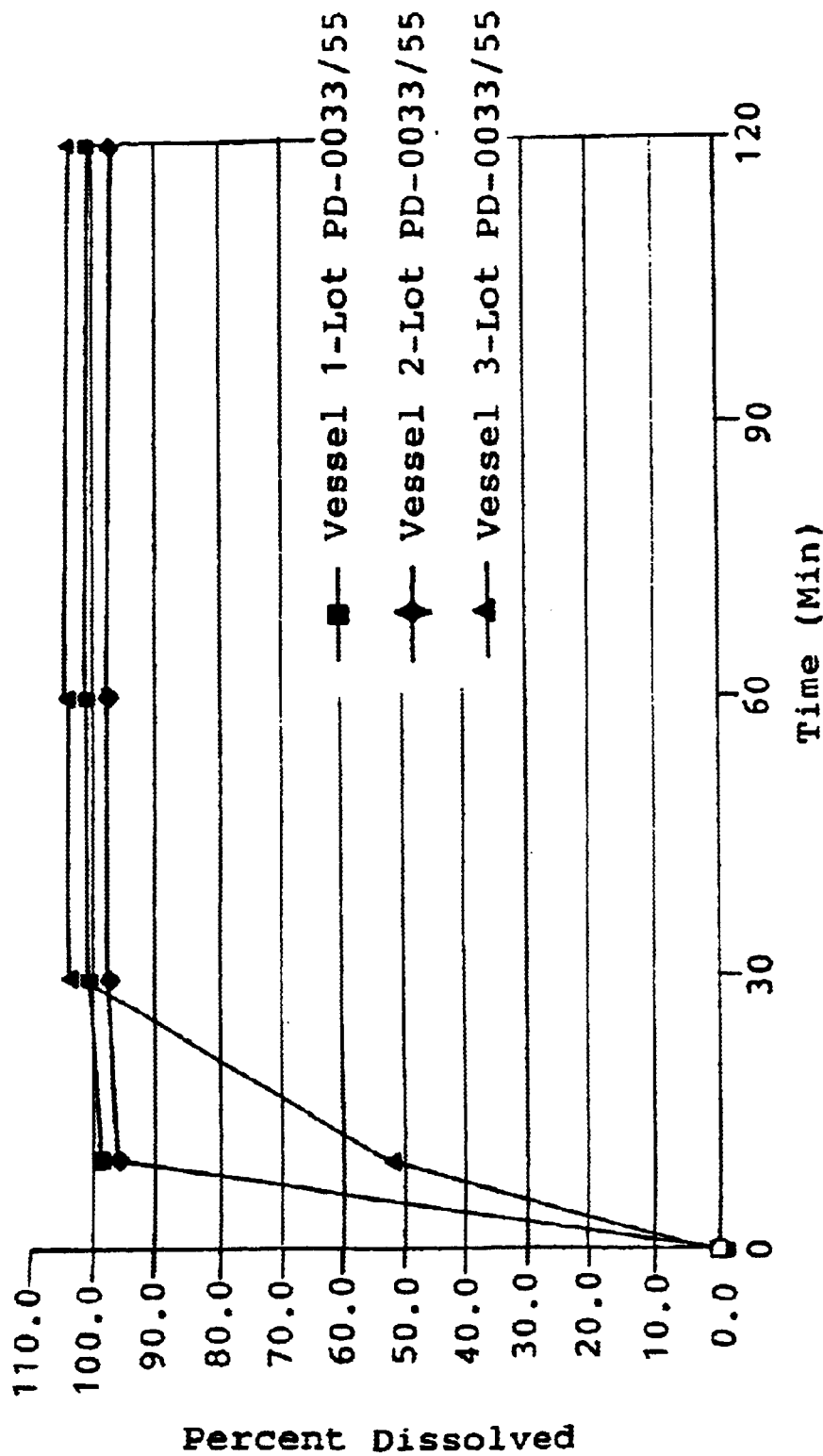
FIG. 18 is a plot of acyclovir-containing tablet percent dissolution over time for the Formulation PD0033-55 from Example 6.

FIG. 18 is a plot of acyclovir-containing tablet percent dissolution over time for the Formulation PD0033-55 from this Example. It presents dissolution results from 100 mg acyclovir tablets containing coated beadlets. The coated beadlets contain 60% acyclovir and are Tween 20 based.

EXAMPLE 7

TABLE 23

Formulations of Acyclovir Enteric Coated Tablets

| Formulation | PD0033-67B | PD0030-67C |
|---|---|---|
| Acyclovir, USP | 25.110 | 25.110 |
| compritol 888 ATO, NF | 11.300 | 11.300 |
| Labrasol, EP | 4.185 | — |
| Tween 20, USP | — | 4.185 |
| SLS, NF/USP | 1.348 | 1.348 |
| Citric Acid, Anhydrous, USP | 0.419 | 0.419 |
| Cab-O-Sil M5, NF | 0.884 | 0.884 |
| Opadry II, Clear, NF | 4.650 | 4.650 |
| Avicel PH301, NF | 31.62 | 28.83 |
| Lactose 316, NF/USP | 9.300 | 9.300 |
| Ac-Di-Sol, USP | 1.860 | 1.860 |
| Stearic Acid, USP | 1.860 | 3.720 |
| Mg Stearate | 0.465 | 1.395 |
| Eudragit L30D-55, NF | 4.375 | 4.375 |
| Triethyl Citrate, NF | 0.437 | 0.437 |
| Talc, USP | 2.188 | 2.188 |
| Total | 100.00 | 100.00 |

Figure 19:
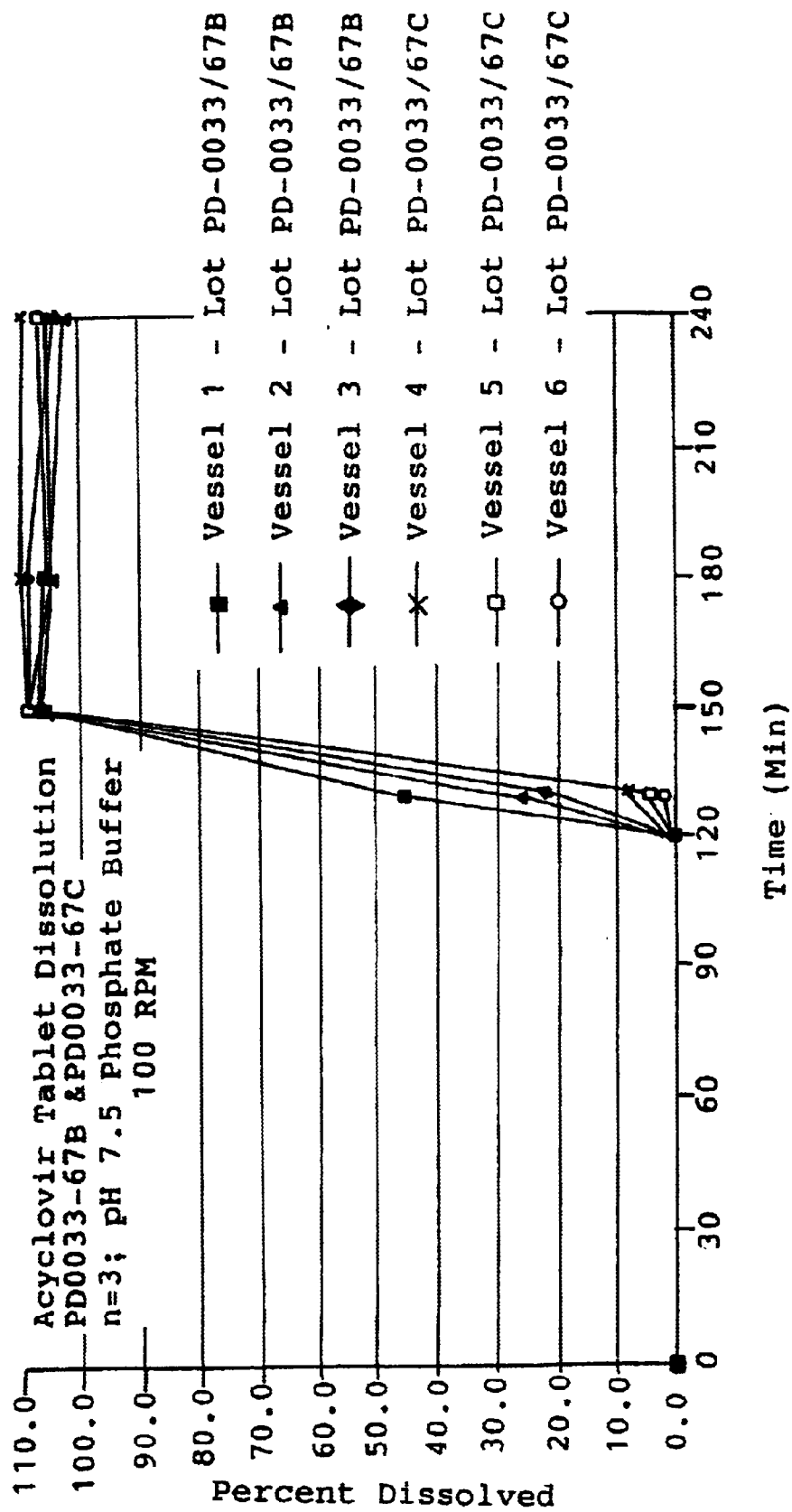
FIG. 19 is a plot of acyclovir-containing tablet percent dissolution over time for two of the Formulations from Example 7.

FIG. 19 is a plot of acyclovir-containing tablet percent dissolution over time for two of the Formulations from this Example. It presents dissolution results for 150 mg enteric coated acyclovir tablets containing coated beadlets made using either Tween 20 to Labrasol® surfactants in combination with 27% Compritrol 888 ATO.

EXAMPLE 8

The acyclovir beadlets were prepared by a spray-congealed method. The stearic acid or Myvaplex 600 was melted in a stainless steel vessel. The other ingredients, except acyclovir powder, were then added into the molten solution of the wax while stirring. Finally, acyclovir was dispersed into the above molten solution at the temperature above the melting point of the mixture. The molten dispersion was pumped to a portable spray-dryer unit and atomized by a dual-fluid nozzle. The congealed product was collected either on the bottom of the chamber or in the cyclone.

TABLE 24

Formulation Of Acyclovir Beadlets Prepared By a Spray-Congealed Method

| Ingredient | PD0022-37 | PD0022-38 |
|---|---|---|
| Acyclovir | 25 | 25 |
| Stearic Acid |  | 50 |
| Myvaplex 600 | 50 |  |
| Labrasol | 12 | 12 |
| Labrafac CM10 | 3 | 3 |
| Gelucire 50/13 | 10 | 10 |
| TOTAL | 100 | 100 |

Figure 20:
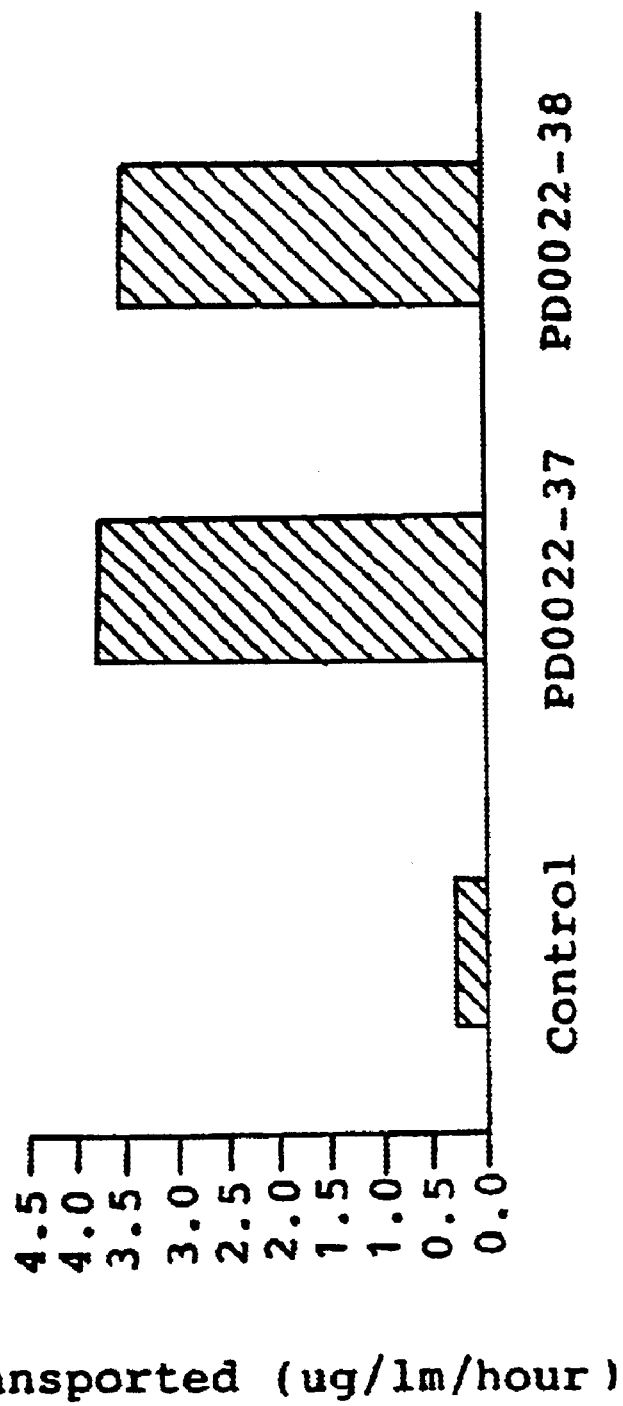
FIG. 20 shows drug transport across Caco-2 cells from acyclovir beadlet formulation shown in Example 8. The beadlets were prepared by a spray-congealed method.

FIG. 20 shows levels of drug transport in the Caco-2 cell model of the above prepared beadlets. Both the PD0022-37 formulation with Myvaplex 600 and the PD0022-38 formulation continuing stearic acid provided enhanced drug transport levels over the control.

EXAMPLE 9

Preparation of Drug-Containing Granules for Amphetamine Base and Salts, Derivatives and their Combinations The following formulation was used to prepare amphetamine granules. The drugs and other ingredients were charged into a fluid bed processor (GPCG-5, Glatt). The molten components (Myvaplex 600 and Tween 20) were sprayed onto the fluidized powder bed under suitable conditions. The resulting granules were then coated with Opadry II. The drug-loaded granules can be further coated with enteric polymers or sustained release polymers. The final dosage form for the granules can be a capsule or a tablet.

TABLE 25

| Core Formulation | % |
|---|---|
| Amphetamine salts | 15.00 |
| Xylitol | 28.00 |
| Explotab | 20.00 |
| Citric Acid | 5.00 |
| Myvaplex 600 | 20.00 |
| Tween 20 | 6.00 |
| Opadry II | 5.00 |
| Cab-O-Sil | 1.00 |
| Total | 100.00 |
| Core Preparation | Hot-melt |
| Form | Granules |
| Size (estimated) | ~400 μm |

EXAMPLE 10

TABLE 26

| Formulation | Uncoated Single Phase Beadlets | | | |
|---|---|---|---|---|
|  | A | B | C | D |
| Calcitonin Sodium | 0.2 |  |  |  |
| Beclomethasone Dipropionate |  | 5 |  |  |
| Testosterone |  |  | 2 |  |
| Alendronate Sodium |  |  |  | 8 |
| Lactose | 29.8 |  | 46 | 21 |
| Compritol 888 ATO | 48 | 48 | 30 |  |
| Myvaplex 600 |  | 46 | 10 | 50 |
| Tween 20 | 20 |  |  |  |
| Labrasol |  |  | 10 | 20 |
| SLS | 1 | 1 | 1 | 1 |
| Citric Acid | 1 |  | 1 |  |
| Total | 100 | 100 | 100 | 100 |
| Core Preparation | Spray-melt | Spray-cong | Hot-melt | Spray-melt |
| Form | Beadlets | Beadlets | Beadlets | Beadlets |
| Size (estimated) | Large | <100 um | Large | Large |

Method of Preparation

Formulations A and D: The spray-melt method is performed in a fluid bed. Solid ingredients including the active ingredients, lactose Compritol 888 ATO, Myvaplex 600, SLS, and citric acid, are placed in a suitably configured fluid bed. Liquid surfactants, i.e., Tween 20 and Labrasol, are then sprayed onto the solid ingredients in the fluid bed to form granules. In the case of calcitonin sodium, lactose triturate is prepared to ensure content uniformity.

Formulation B: The waxy materials are melted in a suitable mixing vessel and all other ingredients are mixed in the melted wax. The mixture is sprayed into a spray-congealer or fluid bed processor to solidify the beadlets.

Formulation C: The hot-melt method is performed in a fluid bed. Solid ingredients including the active ingredient, lactose, SLS, and citric acid, are placed in a fluid bed. The melted waxes with liquid surfactant are then sprayed onto the solid ingredients in the fluid bed to form granules.

What is claimed is:

1. A composition comprising:
   at least one therapeutic agent and a solid beadlet having a size of from 50 microns to 1,000 microns, said beadlet comprising at least 20% by weight of at least one hydrophobic long chain fatty acid or glycerol ester thereof having 12 to 22 carbon atoms and at least 3.0% by weight of at least one surfactant, said at least one surfactant being a liquid at room temperature, said at least one surfactant being selected from the group consisting of ethylene or propylene oxide block copolymers, polyglycolyzed glycerides, sorbitan esters of stearate, sorbitan esters of laurate, polyethylene-polypropylene glycol block copolymers, sucrose long chain carboxylic acid esters, sucrose monoglycerides, sucrose diglycerides, sorbitan monoglycerides, sorbitan diglycerides. PEG derivatives of caprylic/capric acid triglycerides, and mixtures thereof, and said therapeutic agent being dispersed in said beadlet.

2. The composition of claim 1 wherein:
   the surfactant is present in an amount from about 3.0% to about 40% by weight; and;

said at least one therapeutic agent is present in an amount from about 0.1% to about 70% by weight.

3. The composition of claim 1, wherein the hydrophobic long chain fatty acid or glycerol ester thereof has a melting point of from about 40 to about 100° C.

4. The composition of claim 1, wherein the hydrophobic long chain fatty acid or glycerol ester thereof is glyceryl behenate.

5. The composition of claim 1 wherein said beadlet as a particle size hat does not exceed 500 microns.

6. The composition of claim 2 wherein said beadlet has a particle size from 100 microns to 350 microns.

7. The composition of claim 1 which further comprises sodium $C_9$–$C_{30}$ alkyl sulfate or citric acid.

8. The composition of claim 1 which includes a fumed colloidal silicon dioxide glidant.

9. The composition of claim 1 wherein the therapeutic agent is acyclovir.

10. The composition of claim 1 wherein the therapeutic agent is dihydroergotamine.

11. The composition of claim 1 wherein the therapeutic agent is methylphenidate.

12. The composition of claim 1 which is coated with an immediate release, sustained-release or enteric-release coating.

13. The composition of claim 1 wherein the therapeutic agent is peptide, protein, or an analog thereof.

14. The composition of claim 1 wherein the therapeutic agent is selected from the group consisting of LHRH, TRH, vasopressin, leuprolide, desmopressin, calcitonin, parathyroid hormone, erythropoietin, enkephalin, growth hormone and interferon.

15. The composition of claim 1 wherein the therapeutic agent is an immunoactive agent elected from the group consisting of peptides, proteins, glycopolysaccharides and glycoproteins, as well as fragments and analogs with similar immunoactivity and at least 90% structural homology to the analog or fragment.

16. A pharmaceutical composition which comprises a plurality of the solid beadlet of claim 1 in a pharmaceutically acceptable carrier.

17. The composition of claim 16 wherein the beadlets contain a therapeutic agent selected from the group consisting of LHRH, leuprolide, desmopressin, calcitonin, parathyroid hormone and erythropoietin.

18. The composition of claim 16 which includes a fumed colloidal silicon dioxide glidant.

19. The composition of claim 16 which is in the form of a tablet.

20. The composition of claim 16 which is in the form of a buccal tablet.

21. The composition of claim 16 which is in the form of encapsulated single phase solid solution beadlets.

22. The composition of claim 1 wherein the surfactant is selected from t group consisting of polyglycolized glycerides, sorbitan esters of laurate, ethylene or propylene block copolymers or combinations thereof.

23. The composition of claim 22 wherein the surfactant is polyoxyethylene 20 sorbitan monolaurate.

* * * * *